United States Patent [19]

Viola et al.

[11] Patent Number: 5,474,223
[45] Date of Patent: Dec. 12, 1995

[54] SURGICAL FASTENER APPLYING APPARATUS

[75] Inventors: Frank J. Viola, Sandy Hook; John C. Robertson, Bloomfield, both of Conn.

[73] Assignee: United States Surgical Corporation, Norwalk, Conn.

[21] Appl. No.: 270,722

[22] Filed: Jul. 5, 1994

Related U.S. Application Data

[63] Continuation of Ser. No. 959,275, Oct. 9, 1992, abandoned, which is a continuation-in-part of Ser. No. 779,505, Oct. 18, 1991, abandoned, and a continuation of Ser. No. 779,097, Oct. 18, 1991, abandoned.

[51] Int. Cl.[6] .................................................. A61B 17/115
[52] U.S. Cl. .......................... 227/179; 227/19; 227/175
[58] Field of Search ............................ 227/19, 179, 175, 227/176, 129

[56] References Cited

U.S. PATENT DOCUMENTS

| | | |
|---|---|---|
| 3,079,608 | 3/1963 | Babkin . |
| 3,080,564 | 3/1963 | Strekopytov et al. . |
| 3,193,165 | 7/1965 | Akhalaya et al. . |
| 3,252,643 | 5/1966 | Strekopytov et al. . |
| 3,388,847 | 6/1968 | Kasulin et al. . |
| 3,552,626 | 1/1971 | Astafiev et al. . |
| 3,593,903 | 7/1971 | Astafiev et al. . |
| 3,692,224 | 9/1972 | Astafiev et al. . |
| 3,795,034 | 3/1974 | Strekopytov et al. . |
| 3,822,818 | 7/1974 | Strekopytov et al. . |
| 4,111,206 | 9/1978 | Vishnevsky et al. . |
| 4,198,982 | 4/1980 | Fortner et al. . |
| 4,207,898 | 6/1980 | Becht . |
| 4,289,133 | 9/1981 | Rothfuss . |
| 4,304,236 | 12/1981 | Conta et al. . |
| 4,305,539 | 12/1981 | Korolkov et al. . |
| 4,319,576 | 3/1982 | Rothfuss . |
| 4,351,466 | 9/1982 | Noiles . |
| 4,379,457 | 4/1983 | Gravener et al. . |
| 4,442,964 | 4/1984 | Becht . |
| 4,473,077 | 9/1984 | Noiles et al. . |
| 4,476,863 | 10/1984 | Kanshin et al. . |
| 4,485,817 | 12/1984 | Swiggett . |

(List continued on next page.)

FOREIGN PATENT DOCUMENTS

| | | |
|---|---|---|
| 908529 | 8/1972 | Canada . |
| 1136020 | 1/1982 | Canada . |
| 0152382 | 8/1985 | European Pat. Off. . |
| 0173451 | 3/1986 | European Pat. Off. . |
| 0503689 | 9/1992 | European Pat. Off. . |
| 1461464 | 12/1966 | France . |
| 1588250 | 4/1970 | France . |
| 2443239 | 12/1979 | France . |
| 1835500 | 4/1961 | Germany . |
| 3301713 | 11/1989 | Germany . |
| 7711347 | 10/1977 | Netherlands . |
| 119846 | 3/1958 | U.S.S.R. . |
| 1185292 | 3/1970 | United Kingdom . |
| 2016991 | 9/1979 | United Kingdom . |
| 2070499 | 9/1981 | United Kingdom . |
| 8706448 | 11/1987 | WIPO . |
| 8900406 | 1/1989 | WIPO . |
| 9006085 | 6/1990 | WIPO . |

OTHER PUBLICATIONS

Information Booklet for Auto Suture® EEA™ Surgical Stapling Instrument, 1984, United States Surgical Corporation.

*Primary Examiner*—Rinaldi I. Rada

[57] ABSTRACT

A surgical apparatus for applying staples or fasteners to tissue to form a circular anastomosis having an adjustable closure mechanism to rapidly approximate the distance between the anvil member and the fastener assembly of the instrument. The adjustable closure mechanism provides for rapid approximation during an initial movement and for fine adjustment of the distance between the anvil member and the fastener assembly upon subsequent movement of the closure mechanism. The closure mechanism consists of an advancing mechanism which operates in a two stage advancement, such that initial movement of the advancing mechanism moves the anvil member a greater distance than a subsequent movement of the advancing mechanism.

19 Claims, 24 Drawing Sheets

U.S. PATENT DOCUMENTS

| | | |
|---|---|---|
| 4,488,523 | 12/1984 | Shichman . |
| 4,505,272 | 3/1985 | Utyamyshev et al. . |
| 4,505,414 | 3/1985 | Filipi . |
| 4,513,746 | 4/1985 | Aranyi et al. . |
| 4,527,724 | 7/1985 | Chow et al. . |
| 4,573,468 | 3/1986 | Conta et al. . |
| 4,576,167 | 3/1986 | Noiles . |
| 4,585,153 | 4/1986 | Failla et al. . |
| 4,589,413 | 5/1986 | Malshev et al. . |
| 4,591,085 | 5/1986 | DiGiovanni . |
| 4,592,354 | 6/1986 | Rothfuss . |
| 4,603,693 | 8/1986 | Conta et al. . |
| 4,605,004 | 8/1986 | DiGiovanni et al. . |
| 4,606,343 | 8/1986 | Conta et al. . |
| 4,606,344 | 8/1986 | DiGiovanni . |
| 4,606,345 | 8/1986 | Dorband et al. . |
| 4,607,636 | 8/1986 | Kula et al. . |
| 4,615,474 | 10/1986 | Strekopytov et al. . |
| 4,617,928 | 10/1986 | Alfranca . |
| 4,646,745 | 3/1987 | Noiles . |
| 4,671,445 | 6/1987 | Barker et al. . |
| 4,681,108 | 7/1987 | Rosati et al. . |
| 4,700,703 | 10/1987 | Resnick et al. . |
| 4,708,141 | 11/1987 | Inoue et al. . |
| 4,741,336 | 5/1988 | Failla et al. . |
| 4,752,024 | 6/1988 | Green et al. . |
| 4,754,909 | 7/1988 | Barker et al. . |
| 4,817,847 | 4/1989 | Redtenbacher et al. . |
| 4,848,637 | 7/1989 | Pruitt . |
| 4,893,622 | 1/1990 | Green et al. . |
| 4,903,697 | 2/1990 | Resnick et al. . |
| 4,907,591 | 3/1990 | Vasconcellos et al. . |
| 4,917,114 | 4/1990 | Green et al. . |
| 4,930,503 | 6/1990 | Pruitt . |
| 4,938,408 | 7/1990 | Bedi et al. . |
| 4,941,623 | 7/1990 | Pruitt . |
| 4,957,499 | 9/1990 | Lipatov et al. . |
| 4,964,559 | 10/1990 | Deniega et al. . |
| 5,005,749 | 4/1991 | Aranyi . |
| 5,018,657 | 5/1991 | Pedlick et al. . |
| 5,027,834 | 7/1991 | Pruitt . |
| 5,040,715 | 8/1991 | Green et al. . |
| 5,104,025 | 4/1992 | Main et al. . |
| 5,122,156 | 6/1992 | Granger et al. . |
| 5,137,198 | 8/1992 | Nobis et al. . |
| 5,139,513 | 8/1992 | Segato . |
| 5,197,648 | 3/1993 | Gingold . |
| 5,197,649 | 3/1993 | Bessler et al. . |
| 5,205,459 | 4/1993 | Brinkenhoff et al. . |
| 5,222,963 | 6/1993 | Brinkerhoff et al. . |
| 5,261,920 | 11/1993 | Main et al. . |
| 5,271,543 | 12/1993 | Grant et al. . |
| 5,271,544 | 12/1993 | Fox et al. . |
| 5,292,053 | 3/1994 | Bilotti et al. . |
| 5,309,927 | 5/1994 | Welch . |
| 5,312,024 | 5/1994 | Grant et al. . |
| 5,333,773 | 8/1994 | Main et al. . |

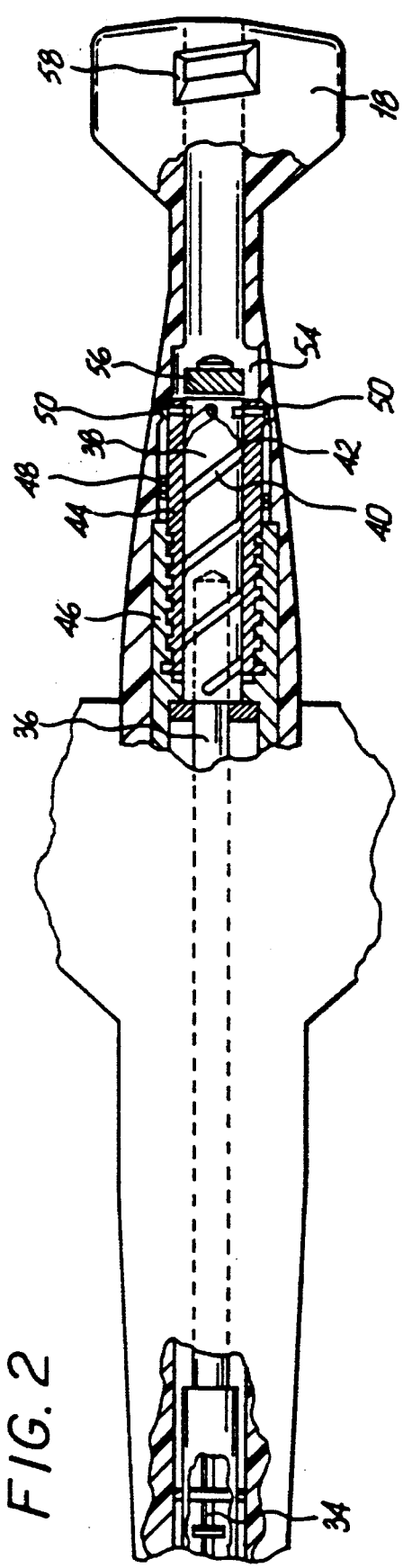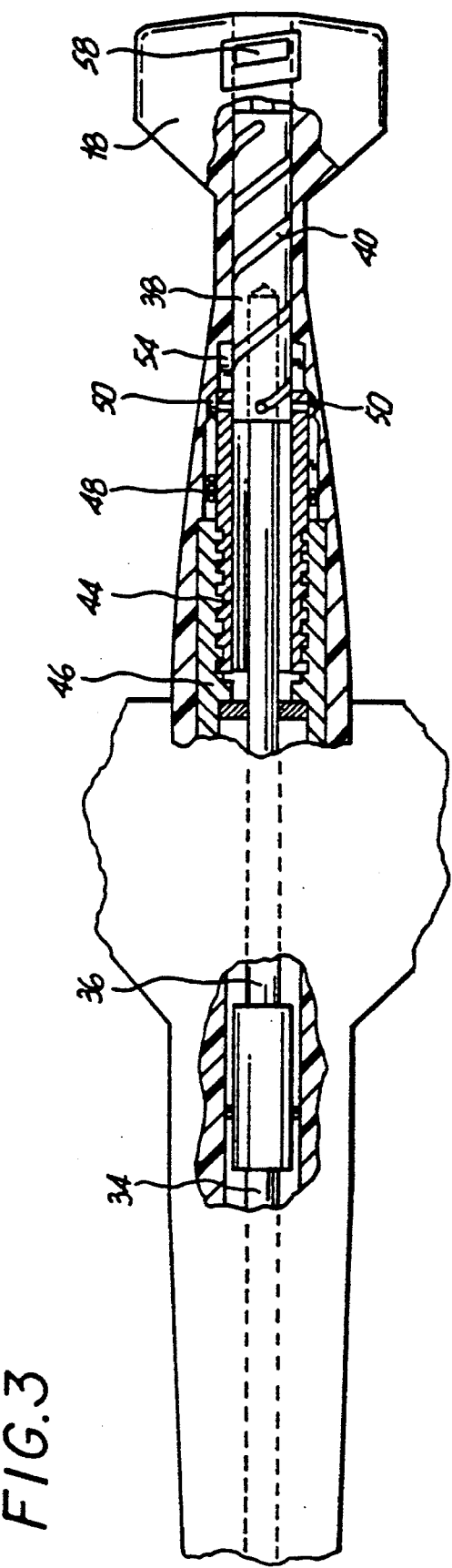

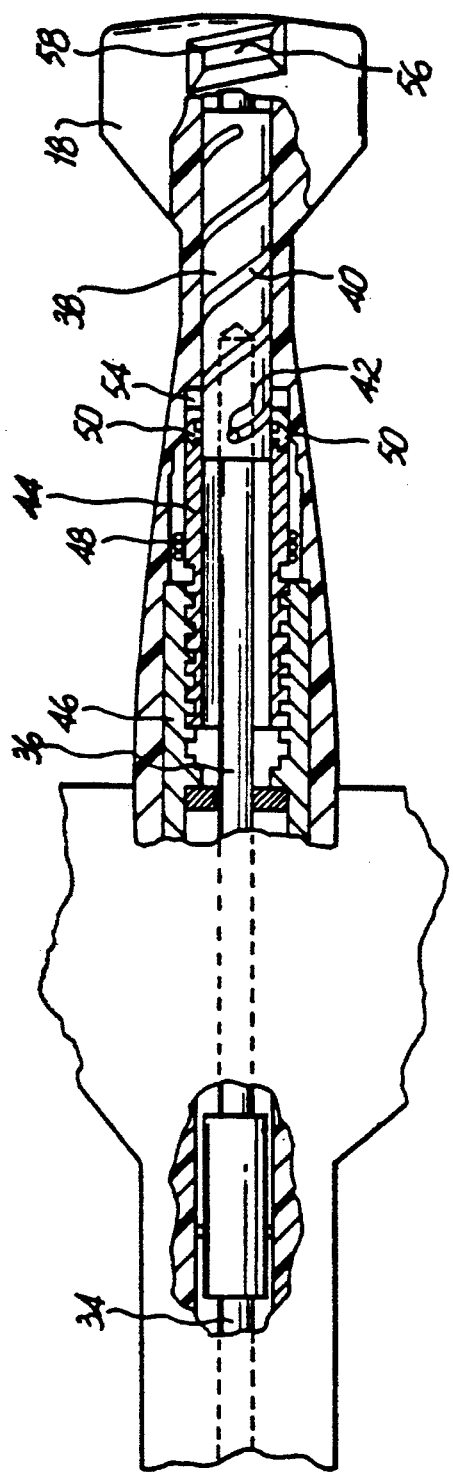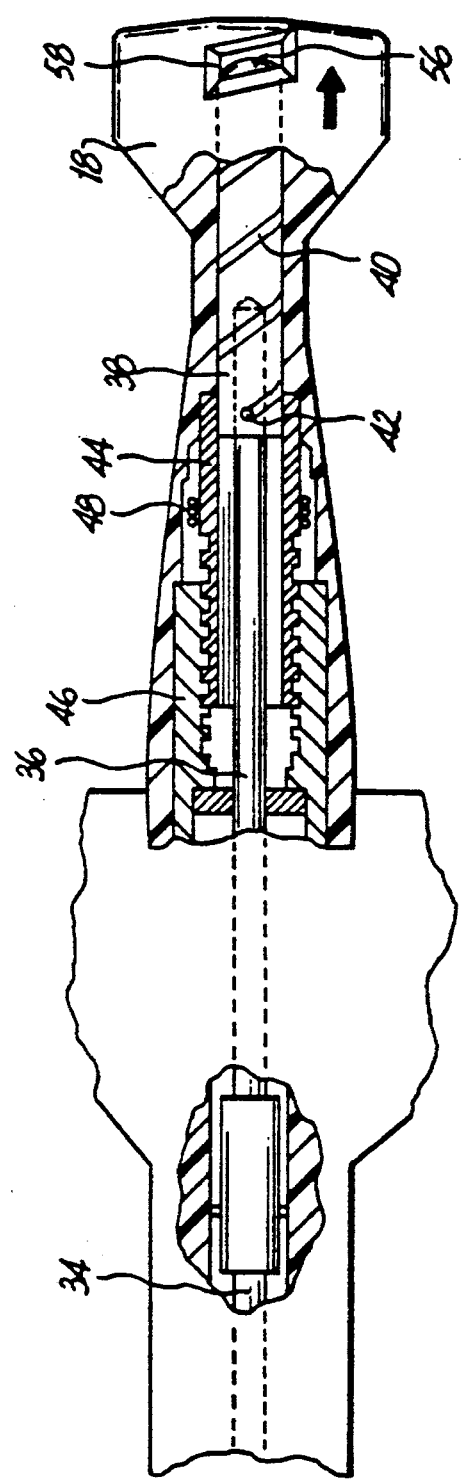

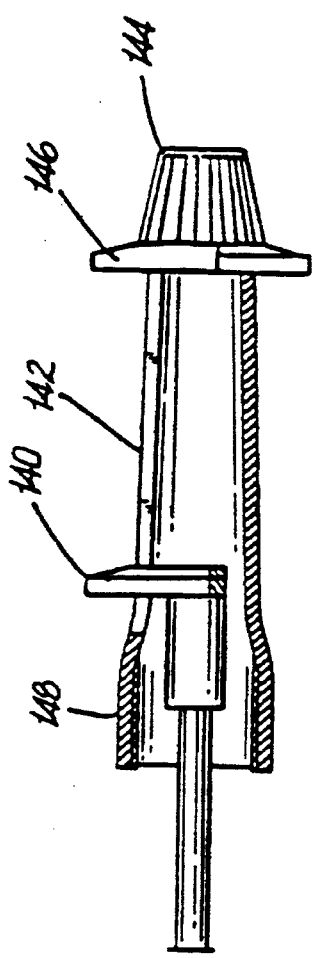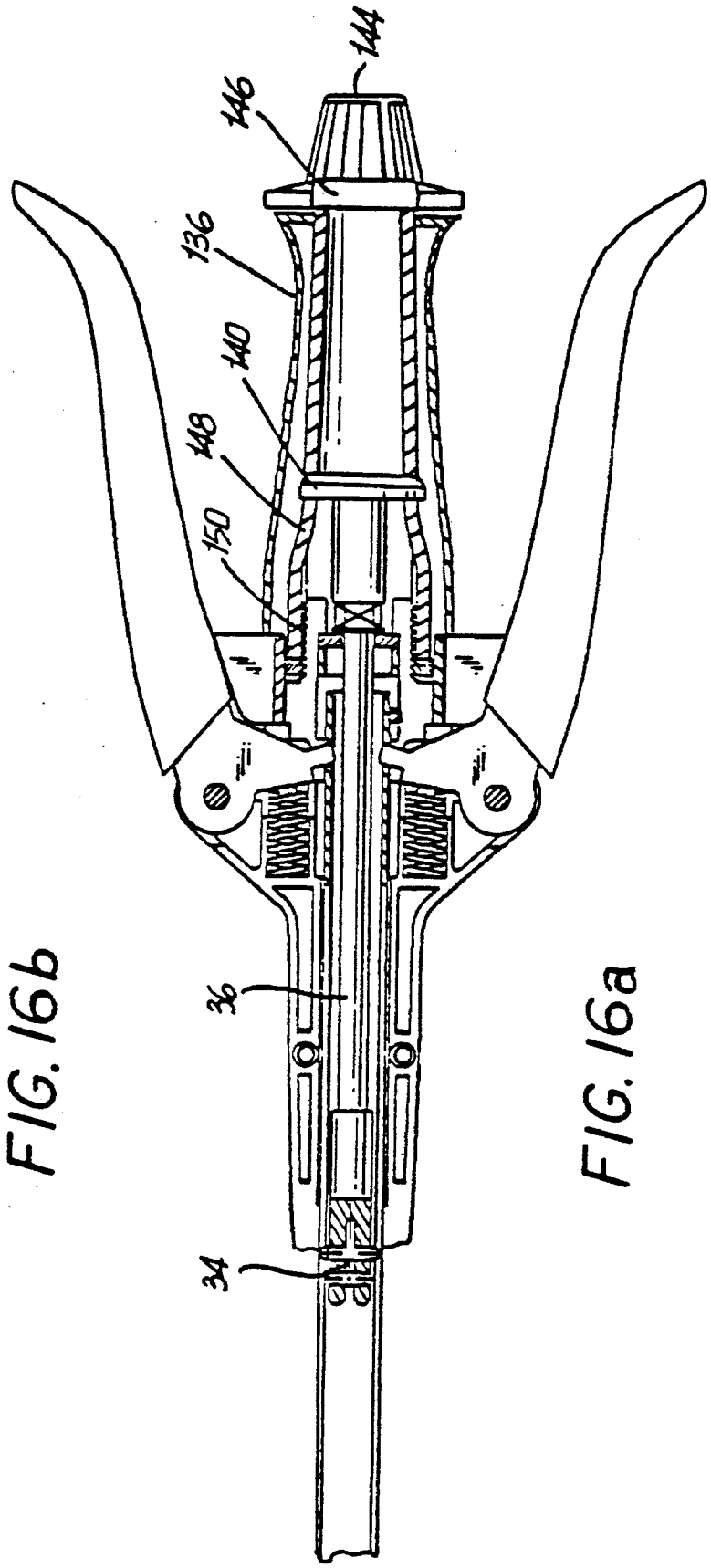

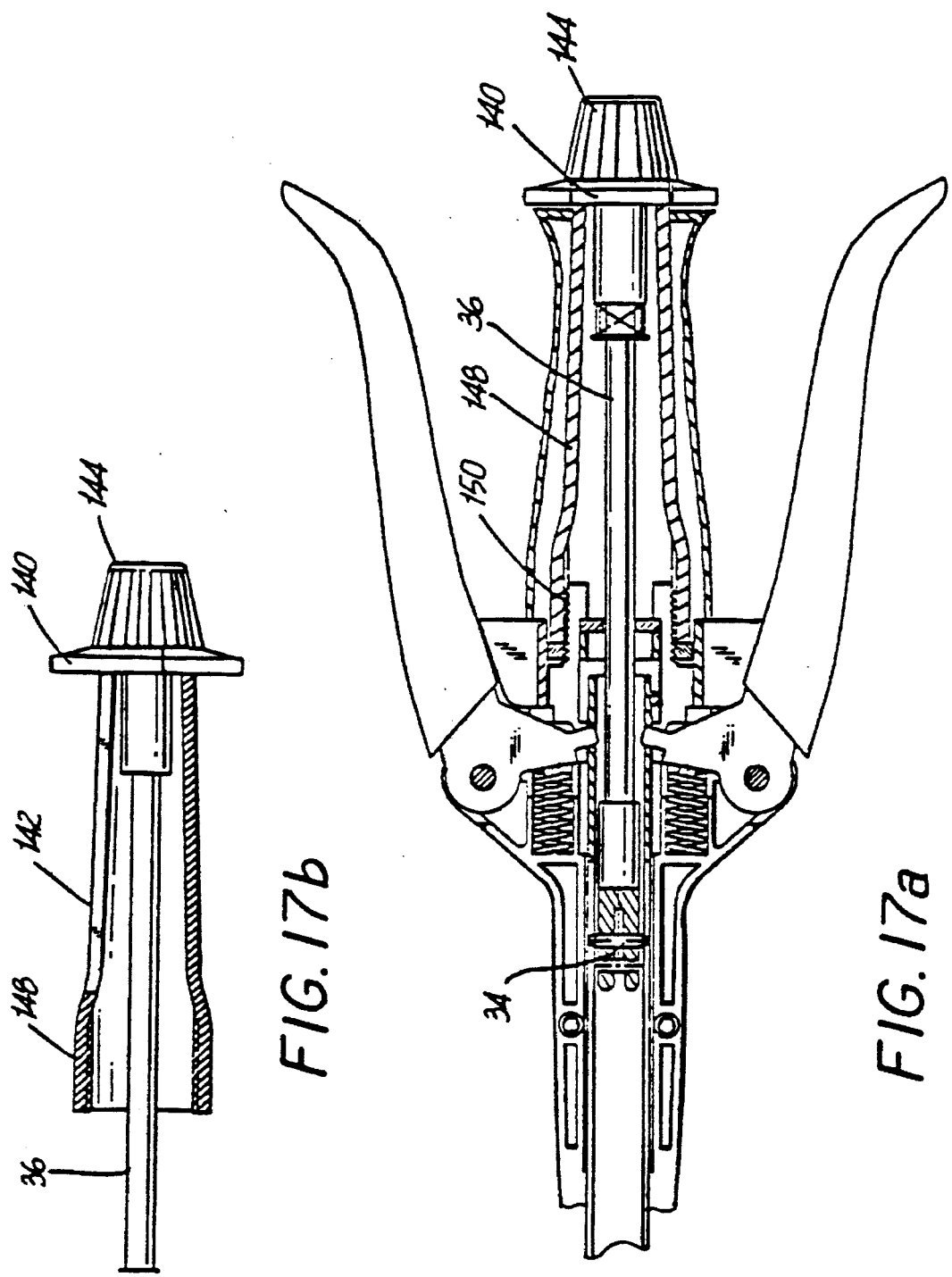

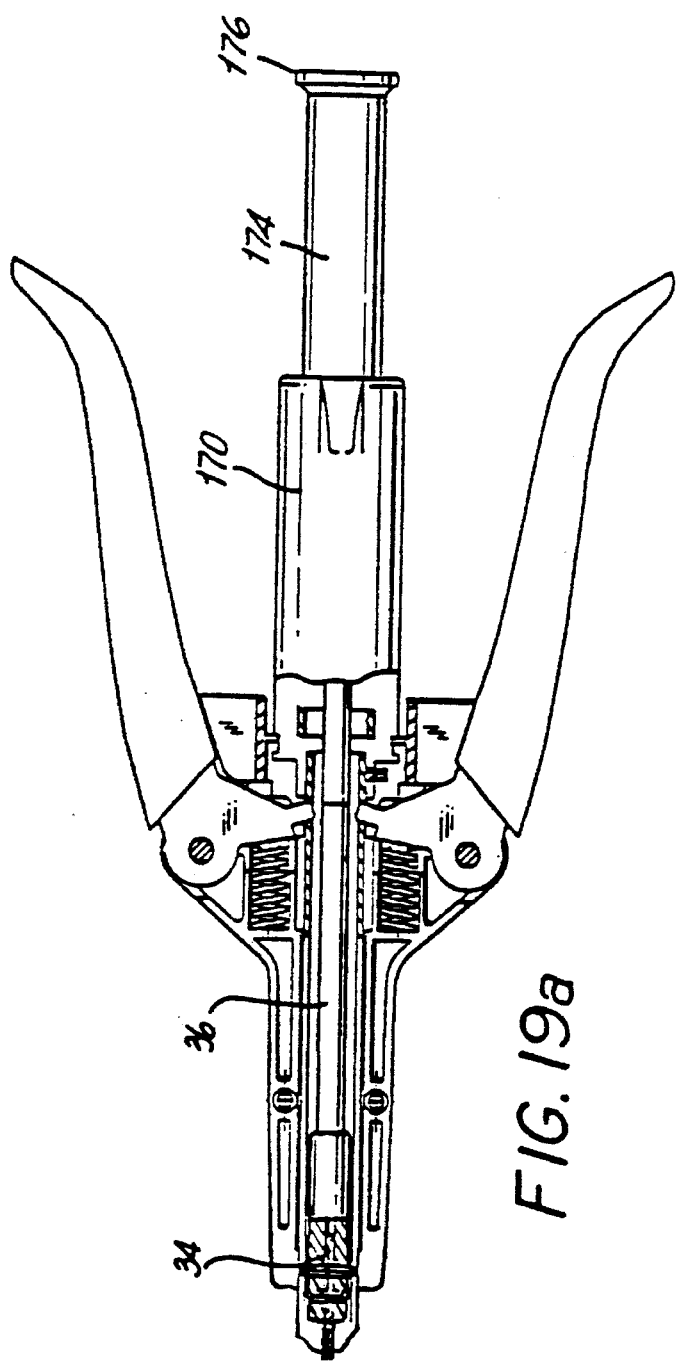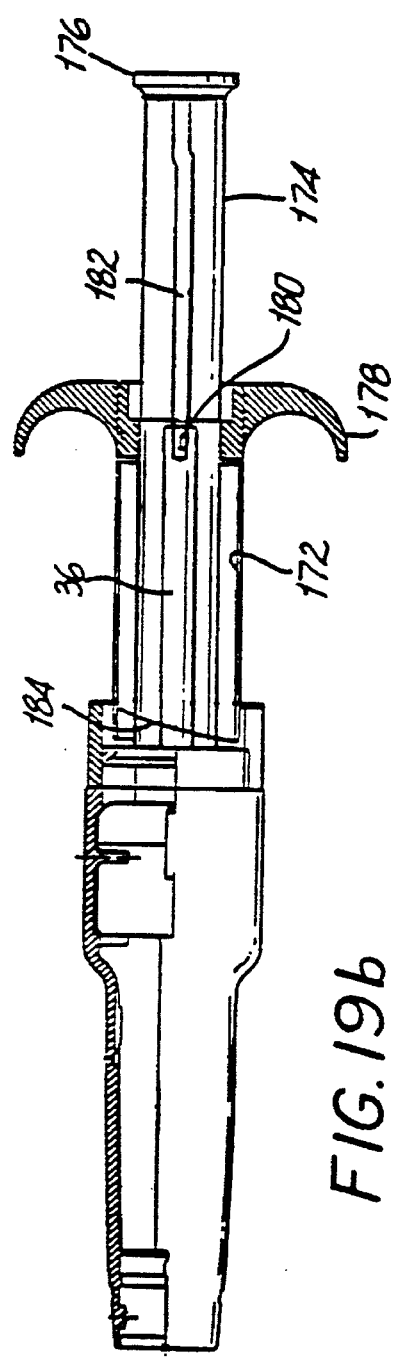

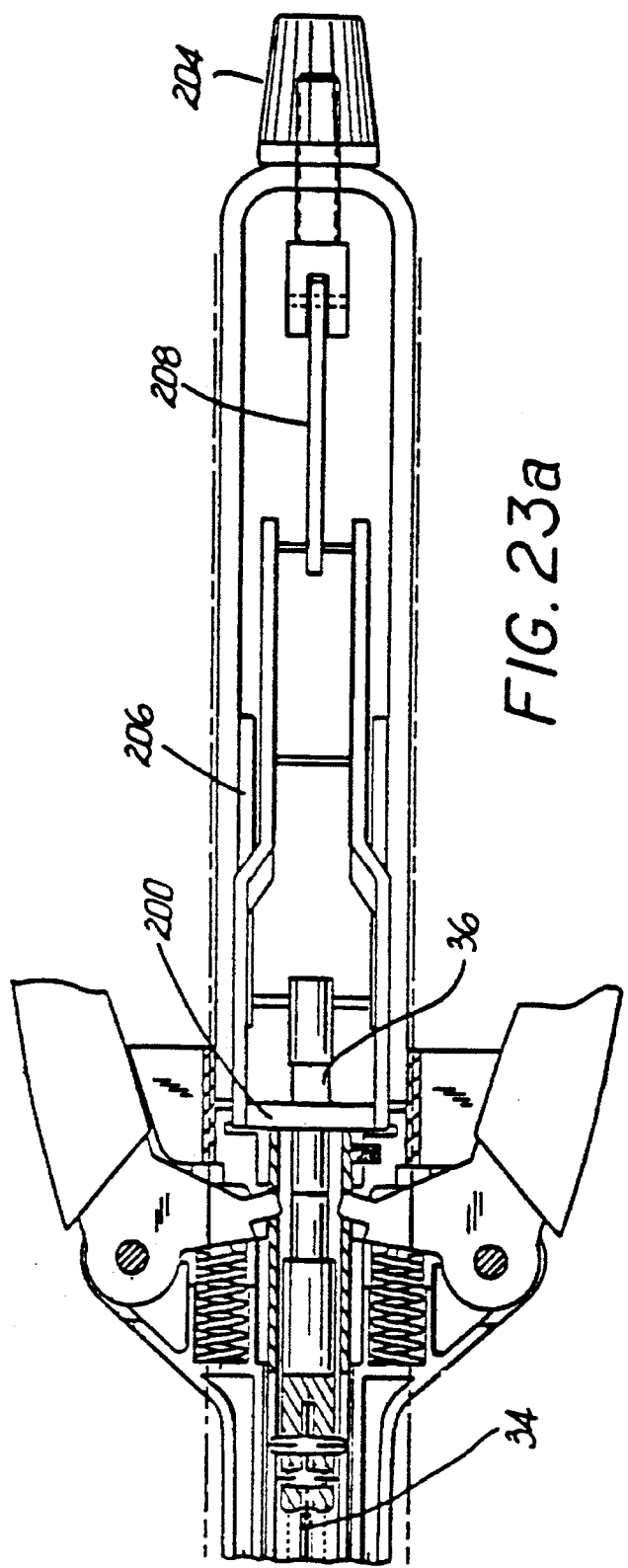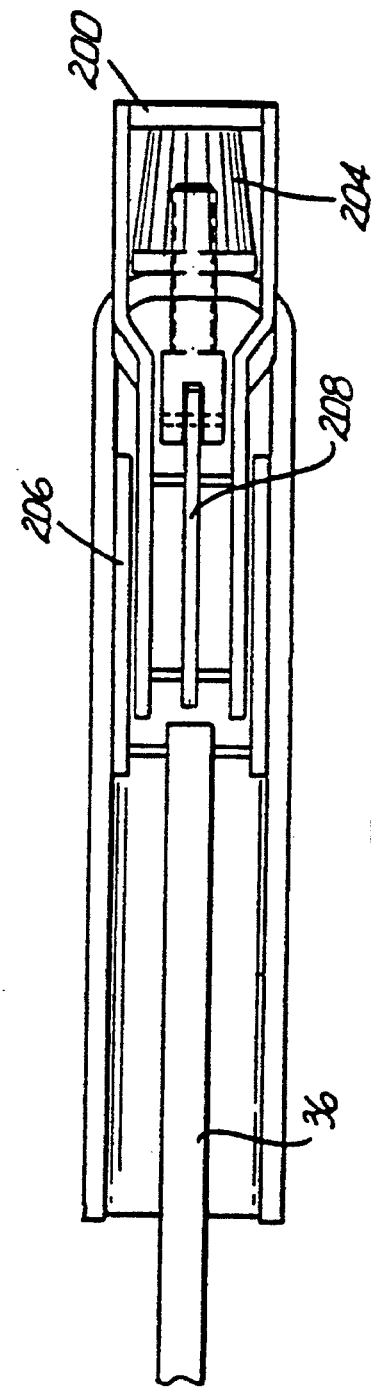

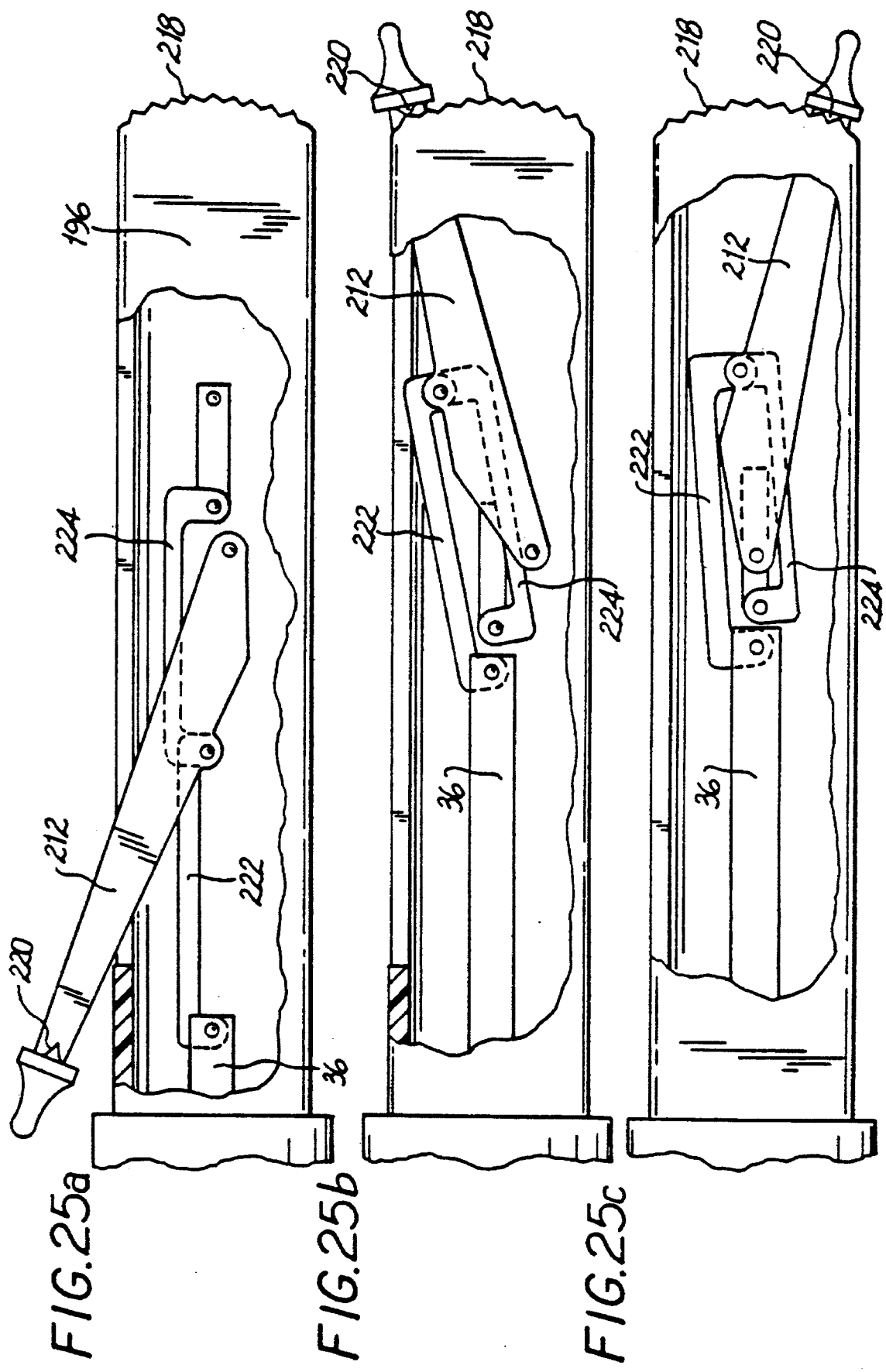

SURGICAL FASTENER APPLYING APPARATUS

CROSS-REFERENCE TO RELATED APPLICATIONS

This is a continuation of U.S. application Ser. No. 07/959,275 filed Oct. 9, 1992, which is acontinuation-in-part of U.S. application Ser. No. 07/779,505 filed Oct. 18, 1991 and a continuation-in-part of U.S. application Ser. No. 07/779,097 filed Oct. 18, 1991 all abandoned.

BACKGROUND OF THE INVENTION

1. Field of the Invention

The present invention relates to surgical instruments for applying surgical fasteners or staples to body tissue, and more particularly to an apparatus for applying an annular array of surgical staples or fasteners. Still more particularly, the invention relates to an apparatus having an adjustable mechanism for controlling the spacing between the staple pusher member and the anvil member between which the tissue is positioned to effect a circular anastomosis.

2. Discussion of the Related Art

Surgical stapling devices for applying an annular array of staples or fasteners to tissue are well known in the art. These devices typically include means for controlling the spacing between the fastener assembly and the anvil member at the distal end of the apparatus. The fastener assembly generally includes a circular array of fasteners such as staples, anastomosis rings, and the like, while the anvil member includes means for completing the circular anastomosis, typically an array of bucket members that clinch the staples after the staples are expelled from the fastener assembly, or may include a locking member for the anastomosis ring. The means for advancing or retracting the anvil in relation to the fastener assembly typically includes a wing-nut type mechanism at a proximal end of the instrument or a rotatable knob member, both of which engage a worm gear arrangement in the handle mechanism to slowly, and methodically advance the anvil member towards the fastener assembly.

Surgical stapling devices for applying an annular array of staples, as well as devices for completing a surgical anastomosis through the provision of anastomosis rings, are well known in gastric and esophageal surgery, for example in classic or modified gastric reconstruction typically formed in an end to end, end to side, or side to side manner. In use, the instrument is positioned within the lumen of an organ such as the stomach, esophagus, or intestine in order to perform the anastomosis. The tissue is positioned between the anvil and the fastener assembly and is typically tied off, for example, by a purse string suture. Thereafter, the anvil member is advanced towards the fastener assembly by rotation of the rotatable knob or wing nut assembly at the proximal end of the instrument to hold the tissue between the anvil member and the fastener assembly. As the staples or the fasteners are expelled from the fastener assembly, a circular knife typically follows the application of the staples to excise unwanted tissue at the anastomosis site. The instrument is then removed from the lumen of the organ.

Closing mechanisms associated with the prior art stapling or fastening devices typically utilize a complex worm gear arrangement or screw bearing member to open and close the spacing between the anvil and the fastener assembly. These devices generally provide a rotatable knob or wing-like assembly remote from the fastener or staple pusher member, and the worm gear mechanism is provided to translate the rotational movement of the knob into longitudinal movement of the anvil member towards the staple pusher member. In order to effect this movement, the surgeon must grasp the device with one hand while rotating the knob or wing-like assembly with the other hand. Because the worm gear is typically a precision component for moving the anvil member in precise increments, it is a time consuming process to move the anvil member a full distance towards the fastener assembly during the surgical procedure. Typical devices require 15 to 20 full 360° rotations of the knob or wing nut assembly to fully close the instrument in order to fire or expel the staples or fasteners into the tissue.

It would be advantageous to expedite the surgical procedure utilizing circular anastomosis instruments. Additionally, although many prior art devices are provided with a visual indicator to signal the surgeon when the anvil has reached a firing position adjacent the staple or fastener assembly, there is generally no indication of the position of the anvil member in relation to the staple assembly until the anvil is immediately adjacent the fastener or staple assembly.

The novel surgical stapling or fastening device for performing a circular anastomosis procedure of the present invention provides an instrument having an adjustable closure mechanism for controlling the spacing between the anvil member and the fastener assembly positioned at the distal end of the instrument. The closing mechanism of the present invention provides a mechanism for both rapidly approximating the distance between the anvil and the fastener assembly, and for incrementally adjusting the remaining distance after the initial rotation. The instrument of the present invention provides a quick and efficient means for approximating the anvil and fastener assembly while including means for accurately positioning the anvil in relation to the fastener assembly to properly set the distance for applying staples or fasteners to the tissue. In addition, the instrument of the present invention allows the surgeon to rapidly move the anvil towards the fastener assembly in a minimal amount of turns so that the surgeon has an indication of the location of the anvil member in relation to the fastener assembly at all times during rotation of the grip member at the handle of the instrument.

SUMMARY OF THE INVENTION

The present invention provides a surgical device for applying an annular array of fasteners such as staples, rings, or the like having a novel mechanism for adjusting the distance between the movable anvil member and the fastener assembly prior to the application of fasteners to body tissue. The adjustable mechanism controls the spacing between the anvil member and the fastener assembly to advance and retract the anvil member to approximate the distance between the anvil and the fastener assembly prior to the activation of the handle mechanism to expel the fasteners or staples from the fastener assembly. The adjustable closure mechanism comprises an advancing means which approximates the distance between the anvil member and the fastener assembly by providing for an initial movement which moves the anvil member over a large distance and further provides for a subsequent movement which moves the anvil member over a shorter distance. The initial movement allows for coarse adjustment of the distance between the anvil member and the fastener assembly, and the subsequent movement provides for fine adjustment of the distance between the anvil member and fastener assembly.

The adjustable closure mechanism of the present invention provides a means for quickly closing the distance between the anvil member and the fastener assembly and further provides means for incrementally adjusting the distance just prior to firing the fasteners from the device.

The adjustable closure mechanism of the present invention may be used with any surgical instrument having a movable anvil member or movable fastener holding member for forming a circular anastomosis positioned at a distal end of the instrument. The adjustable closure mechanism of the present invention expedites the surgical procedure by providing a means for rapidly adjusting the distance between the anvil member and the fastener assembly and further providing a means for fine adjustment of the distance prior to firing. The distance is approximated in a fast and efficient manner to position the anvil in proper alignment for the application of surgical fasteners such as staples, rings or the like.

The apparatus of the present invention comprises a tubular body portion having a staple pusher member disposed at a distal end. The staple pusher member is associated with an annular array of staples and provides means for expelling the staples from the pusher member in response to movement of an actuating means positioned at a proximal end of the tubular body portion. An anvil member is provided opposite the annular array of staples to clinch the staples in the tissue upon expulsion of the staples. The device further comprises means for advancing the anvil member between the extended position away from the staple pusher member and a retracted position adjacent the staple pusher member, where the advancing means moves the anvil member in a two stage advancement. Initial movement of the advancing means advances the anvil member a first distance, while a subsequent movement of the advancing means advances the anvil member a second distance which is less than the first distance caused by the initial movement. The advancing means and the actuating means preferably comprise a handle assembly for the surgical stapler apparatus.

In a preferred embodiment, the means for advancing the anvil member towards the staple pusher member comprises a cam member which is cylindrically shaped and is provided with a helical groove wound about an outer surface of the cam member. The cam member is fixedly secured to an inner rod member which in turn is secured to a flexible member which extends the length of the tubular body portion and terminates at the staple pusher member. The anvil member is preferably removably secured to the flexible member at the staple pusher member.

The handle assembly of the surgical stapler apparatus preferably includes a grip member which extends proximally from the handle assembly and which includes the cam member of the advancing means. The cam member is preferably slidably positioned within the grip member and the helical groove of the cam member is engaged by a pin which is fixedly secured on an inner surface of the grip member. As the grip member is rotated about a longitudinal axis of the apparatus, the pin member rotates with the grip member and causes the helical groove to ride over the pin member to slidably advance and retract the cam member. The slidable movement of the cam member causes the inner rod member to advance and retract, and further causes the flexible member in the tubular body portion to advance and retract. This of course advances and retracts the anvil member to approximate the distance between the anvil member and the staple pusher member.

In the preferred embodiment, a threaded collar member is concentrically positioned about and releasably secured to the cam member, so that the threads of the collar member engage a bushing member which is positioned in the handle assembly. Means for restricting movement of the threaded collar member is provided in the form of pin members which prevent movement of the collar until initial movement of the grip member is completed, i.e. the pin member on the inside surface of the grip member fully travels the helical groove of the cam member and abuts an end of the helical groove. At this time, the retaining pins of the collar member are permitted to drop into countersunk bores in the cam member to remove the restricting means and permit rotation of the threaded collar within the bushing member. The threads of the threaded collar member have a pitch which is less than the pitch of the helical groove, and provides for fine adjustment of the distance between the anvil member and the stapler pusher member to further approximate the anvil member in relation to the staple pusher member.

In use, the grip member is rotated and the helical groove of the cam member rides over the pin on the inside surface of the grip member to rapidly and slidably move the cam member within the grip member. This causes a rapid approximation of the anvil member and rapidly advances the anvil member towards the staple pusher member. Once the pin on the inside surface of the grip member reaches an end of the helical groove, the retaining pins on the threaded collar member are permitted to drop into countersunk bores in the collar and cam member to permit the threaded collar to rotate to further move the anvil member towards the staple pusher member with tissue therebetween. Once the anvil member is a proper distance from the staple pusher member, the surgeon may then fire the staples or fasteners through the tissue to effect a circular anastomosis at that site.

Alternatively, the threaded collar may be eliminated and the cam member provided with a variable pitch so that the initial pitch is greater than the final pitch. This provides for movement of the pin member within the helical groove rapidly during initial rotation of the grip member followed by a fine adjustment stroke during subsequent rotation of the grip member. In a further alternate embodiment, the pin member may be provided on the inner rod member and the helical groove may be positioned on an inner surface of the cam member so that rotation of the grip member moves the inner rod member over the helical groove a large initial distance, and subsequent rotation moves the inner rod member, and consequently the anvil member, shorter distances per rotation of the grip member.

A further embodiment of the present invention provides a grip member having a radially directed slot to accommodate a latch member which is secured to the inner rod member. The latch member is linearly slidable along the grip member to advance and retract the anvil member at the distal end. Fine adjustment of the distance between the anvil member and the staple pusher member is effected by rotation of the grip member when the latch member is fully drawn towards the proximal end of the instrument. Once the latch member is moved to the proximal end of the instrument, the latch member is engaged in a notch in an end knob member which then permits rotation of a cylindrically shaped sleeve member inside the grip member to adjust the final distance between the anvil member and the staple pusher member.

Another embodiment of the present invention provides a grip member which includes at least a pair of telescoping cylinders, one of which is stationary and a second of which is slidably movable in relation to the other cylinder. The movable cylinder is secured to the inner rod member to rapidly advance and retract the anvil member in relation to staple pusher member. Once the initial movement is completed, the movable cylinder, which is further provided with a camming surface at its distal end, is rotatable in relation to the stationary cylinder so that the cam surface engages a bearing surface to provide for fine adjustment between the anvil member and the staple pusher member.

An additional embodiment of the present invention provides a grip member having a lever mechanism which is pivotable in relation to the grip member over the longitudinal axis of the grip member. The lever mechanism rapidly moves the inner rod member, and consequently the anvil member to advance and retract the anvil member in relation to the staple pusher member. Means for fine adjusting the distance between the anvil member and the staple pusher member is provided, and may comprise a rotatable knob member or a ratchet mechanism for fine adjusting the lever mechanism after the initial movement.

In each of the above embodiments, after the fasteners or staples are driven into the tissue, a circular knife positioned at the distal end as part of the staple fastener assembly excises the unwanted tissue and the instrument is quickly removed from the lumen of the organ being repaired. The unwanted tissue is easily removed from the instrument by reversing the advancing means to rapidly move the anvil member away from the staple pusher member.

BRIEF DESCRIPTION OF THE DRAWINGS

The foregoing features of the present invention will become more readily apparent and may be understood by referring to the following detailed description of an illustrated embodiment of the surgical stapling apparatus and its novel adjustable closure mechanism, taken in conjunction with the accompanying drawings, in which:

FIG. 2 illustrates a cross-sectional view of the apparatus of FIG. 1 in which the handle assembly is shown in a position where the anvil member is positioned away from the staple pusher member;

FIG. 3 illustrates a cross-sectional view of the apparatus of FIG. 2 in which an initial movement of the advancing means has been completed;

FIG. 4 illustrates a cross-sectional view of the apparatus of FIG. 2 during a subsequent movement of the advancing means;

FIG. 5 illustrates a cross-sectional view of the apparatus of FIG. 2 after completion of the subsequent movement of the advancing means where the anvil member is positioned adjacent the staple pusher member prior to expelling the staples from the staple pusher member;

FIGS. 6a–6c illustrate the advancing means of the apparatus of FIG. 2, in which FIG. 6a illustrates a plan view of the cam member, FIG. 6b illustrates a plan view of the threaded collar member, and FIG. 6c illustrates a cross-sectional view of the threaded bushing;

FIGS. 16a and 16b illustrate a cross-sectional view of the advancing mechanism of the apparatus of FIG. 15 in which the anvil member is positioned away from the staple pusher member;

FIGS. 17a and 17b illustrate cross sectional views of the apparatus of FIG. 15 showing the position of the advancing means corresponding to the anvil member being positioned adjacent to the staple pusher member;

FIGS. 19a and 19b illustrate partial cross-sectional views of the apparatus of FIG. 18 corresponding to a position where the anvil member is located away from the staple pusher member;

FIGS. 23a and 23b illustrate top schematic views of the advancing means of FIG. 21 before and after actuation;

FIGS. 25a–25c illustrate side schematic views of the lever mechanism of FIG. 24 during actuation.

DETAILED DESCRIPTION OF THE PREFERRED EMBODIMENTS

Figure 1:
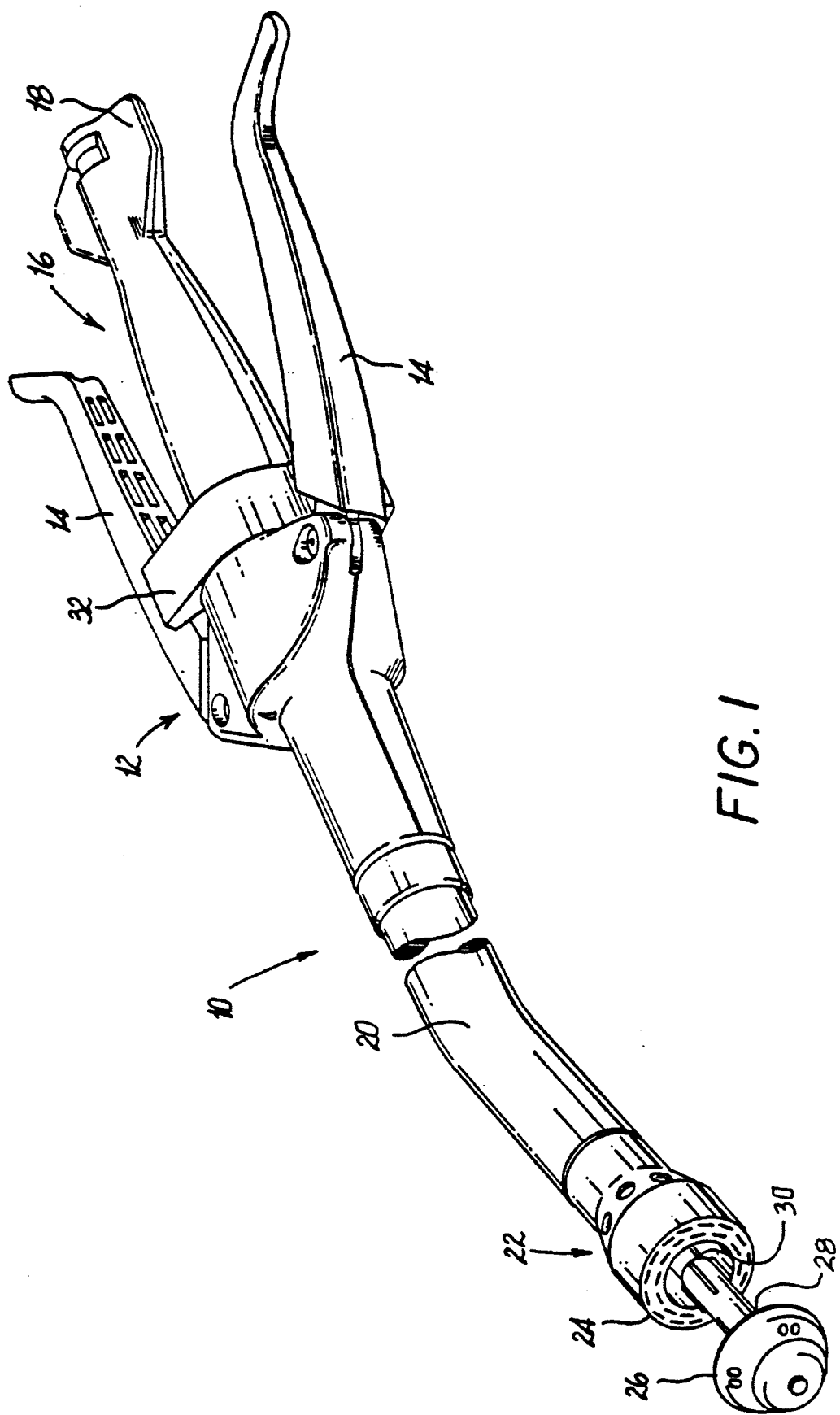
FIG. 1 illustrates a perspective view of the surgical stapling apparatus having the preferred adjustable closure mechanism of the present invention.

Referring now in specific detail to the drawings, in which like reference numerals identify similar or identical elements throughout the several views, FIG. 1 shows a surgical stapling apparatus 10 which employs the adjustable closure mechanism of the present invention. Apparatus 10 includes a handle assembly 12 having at least one pivotable actuating handle member 14, and further includes advancing means 16. Advancing means 16 preferably comprises a rotatable grip member or knob 18 whose function will be described below.

Extending from handle assembly 12, there is provided a tubular body portion 20 which may be constructed so as to have a curved shape along its length. Tubular body portion 20 may also be straight, in other embodiments may be flexible to bend to any configuration. Body portion 20 terminates in staple pusher member 22 which is associated with an annular array of staples 24. Positioned opposite staple pusher member 22 is provided an anvil member 26 which is connected to apparatus 10 by shaft 28 at connection means 30. Anvil member 26 and staple pusher member 22 are disclosed in commonly assigned U.S. Pat. No. 5,119,983, issued Jun. 9, 1992, which is incorporated herein by reference.

While the preferred embodiment of the present invention utilizes a staple pusher member having an annular array of staples positioned on the tubular body portion, and having the anvil member positioned opposite the staple pusher member for movement towards and away from the staple pusher member, it is of course contemplated that the anvil member may be positioned on the tubular body portion and the staple pusher member and array of staples be positioned opposite the anvil member for movement towards and away from the anvil member. Such a construction is to be considered within the scope of the present invention.

FIGS. 2–5 each illustrate a cross-sectional view of the handle assembly 12 of instrument 10 of FIG. 1. FIGS. 2–5 illustrate the operation of the advancing means 16 of the adjustable closure mechanism of the present invention. In particular, FIG. 2 illustrates the positioning of the adjustable closure mechanism which corresponds to the location of the anvil member 26 positioned away from the staple pusher member 22.

As seen in FIG. 2, the adjustable closure mechanism includes a cam member 38 having a helical groove 40 positioned thereon. Cam member 38 is secured to inner rod member 36 which extends through handle assembly 12 and is coupled to flexible member 34. Flexible member 34 is positioned within tubular body portion 20 and is coupled to the connection means 30 within staple pusher member 22 for connection to anvil member 26. Movement of inner rod 36 and flexible member 34 controls the advancing and retracting of anvil member 26.

Figure 6A:
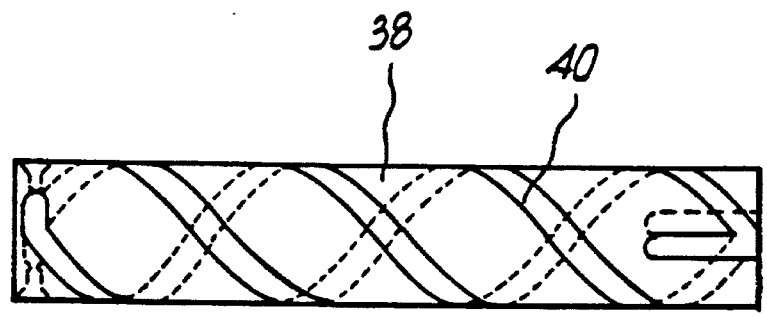
Figure 6B:
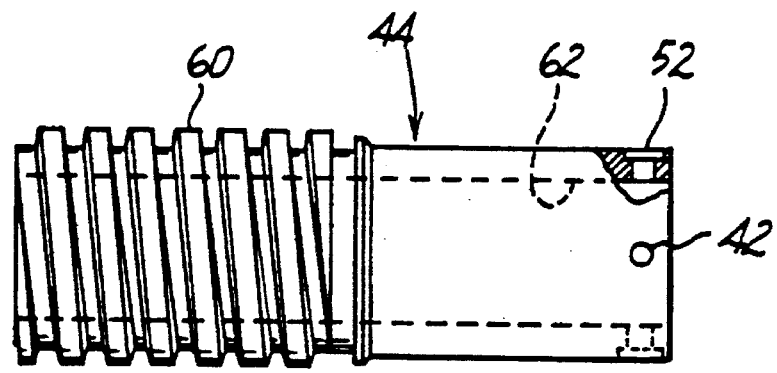
Figure 6C:
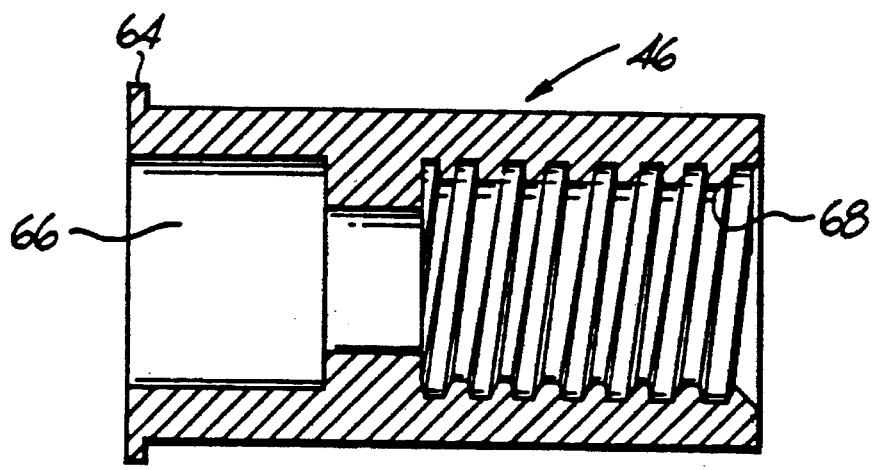

In the embodiment of FIG. 2, the advancing means essentially comprises grip member 18 having cam member 38, threaded collar 44 and bushing member 46 positioned within grip member 18. Cam member 38 is secured to inner rod member 36 by any suitable means to ensure that movement of cam member 38 operatively advances and retracts inner rod member 36. Grip member 18 includes an inwardly directed pin member 42, through collar 44, which is engaged in helical groove 40 of cam member 38. A spring member 48 is secured about threaded collar member 44, whose operation will be described below. As best seen in FIGS. 6a-6c threaded collar 44 is provided with a threaded section 60 which engages the internal threads 68 of bushing member 46. Collar member 44 is provided with an internal passage 62 which slidably accepts cam member 38. Countersink bore holes 52 are provided whose function will be described below. Bushing member 46 also includes an internal passageway 66 and is further provided with a flange member 64 which allows for rotational movement of bushing 46 but prevents longitudinal or axially movement of the bushing.

In operation, the instrument is positioned within a tubular organ in the body of the patient and the ends of the organ to be joined are positioned in the gap between the staple pusher member 22 and the anvil member 26 so that the anvil member 26 is fully extended. As is conventional, the ends of the organ may be secured over the anvil and the staple pusher member by a purse string suture prior to approximation of the anvil member in relation to the staple pusher member. In order to approximate anvil member 26 towards staple pusher member 22, grip member 18 is rotated so that pin member 42 rotates about the longitudinal axis of handle assembly 12. Rotation of pin member 42 causes cam member 38 to begin to move proximally as the helical groove 40 rides over pin member 42. As cam member 38 moves to the position shown in FIG. 3, inner rod member 36 moves proximally with cam member 38, bringing flexible member 34 and anvil member 26 with it. This draws the anvil member 26 into position adjacent staple pusher member 22 and locates the ends of the tissue between these two members. Due to the pitch of helical groove 40, initial rotation of grip member 18 provides for coarse adjustment of the gap or distance between anvil member 26 and staple pusher member 22. The preferred pitch of helical groove 40 allows for approximately two 360° rotations of grip member 18 to approximate anvil member 26 to its position adjacent staple pusher member 22, when cam member 38 is shown in the position as seen in FIG. 3. Cam member 38 allows for rapid approximation of the anvil member 26, and speeds up the surgical procedure by eliminating as many as ten 360° turns of the advancing means of a conventional surgical stapling apparatus.

Once the cam member is in the position shown in FIG. 3, the advancing means of the present invention in this figure provides for fine adjustment of the distance between the anvil member 26 and the staple pusher member 22. When cam member 38 has reached the position shown in FIG. 3, retaining pins 50 are permitted to "drop" into countersunk bore holes 52 in threaded collar 44. When the retaining pins drop into the countersunk bores, it allows threaded collar 44 to begin to advance proximally into bore 54 of grip member 18. As best seen in FIG. 4, continued rotation of grip member 18 tightens spring member 48 about collar 44 to allow collar 44 to begin rotating and sliding in a proximal direction. Bushing 46 is held in place and is allowed only to rotate due to flange 64. As grip member 18 rotates and collar 44 slides rearwardly in bore 54, cam member 38 and inner rod member 36 continued to move rearwardly in a fine adjustable manner due to the threads 60 of threaded collar 44 engaging the inner threads 68 of bushing 46. The precise position of anvil member 26 may be located with respect to staple pusher member 22 by the indicator means on grip member 18, which preferably comprises a colored flag 56 which appears in flag window 58. Once the proper distance is set between anvil member 26 and staple pusher member 22, as shown by the positioning of the advancing means in FIG. 5, and as indicated by the flag 56 being positioned in window 58, interlock means 32 may be released and actuating handles 14 may be pivoted to drive the staples through the tissue against the anvil member to complete the circular anastomosis of the tubular organ.

Figure 7:
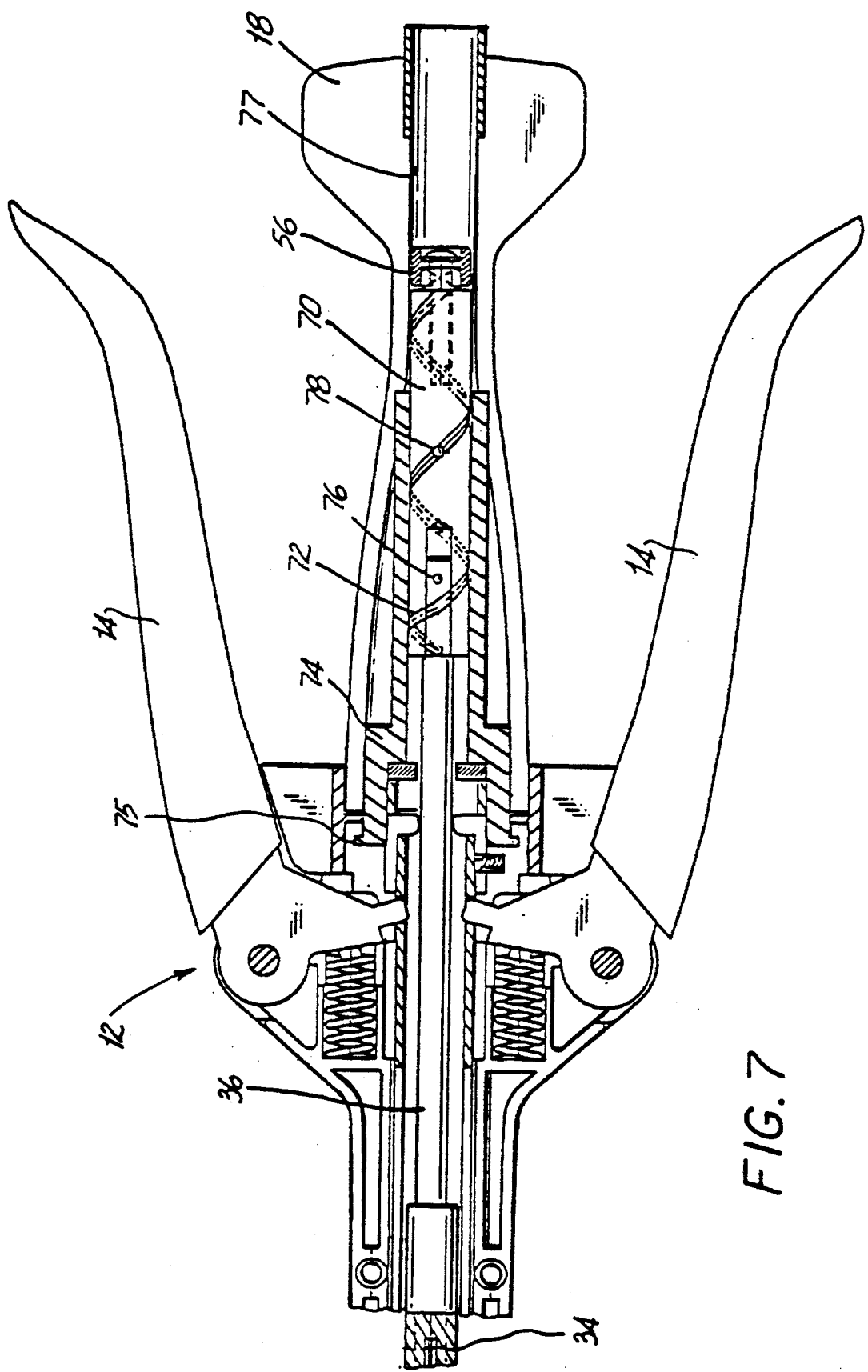
FIG. 7 illustrates a cross-sectional view of an alternate embodiment of the apparatus of FIG. 2 illustrating the advancing means having a variable helical groove, illustrating the position in which the anvil member is located away from the staple pusher member.

FIG. 7 illustrates the handle assembly 12 of the instrument having an alternate embodiment of the advancing means of the present invention. As seen in FIG. 7, cam member 70 is provided with a helical groove 72 having a variable pitch which allows for movement of the anvil member 26 over a first distance as well as movement over a second distance which is less than the first distance upon rotation of grip member 18. FIG. 7 illustrates the cam member 70 in a position which corresponds to the anvil member 26 being positioned away from the staple pusher member 22. Cam member 70 is secured to inner rod member 36 in a conventional manner, such as by connection pin 76. Inner rod member 36, as described above, is secured to flexible member 34 which runs through tubular body portion 20. Cam member 70 fits within rotatable sleeve member 74, which will rotate on rotation of grip member 18, but is prevented from moving longitudinally by flange 75. Sleeve member 74 is provided with a rotation pin 78 which engages helical groove 72. The operation of cam member 70 will now be described.

Figure 8:
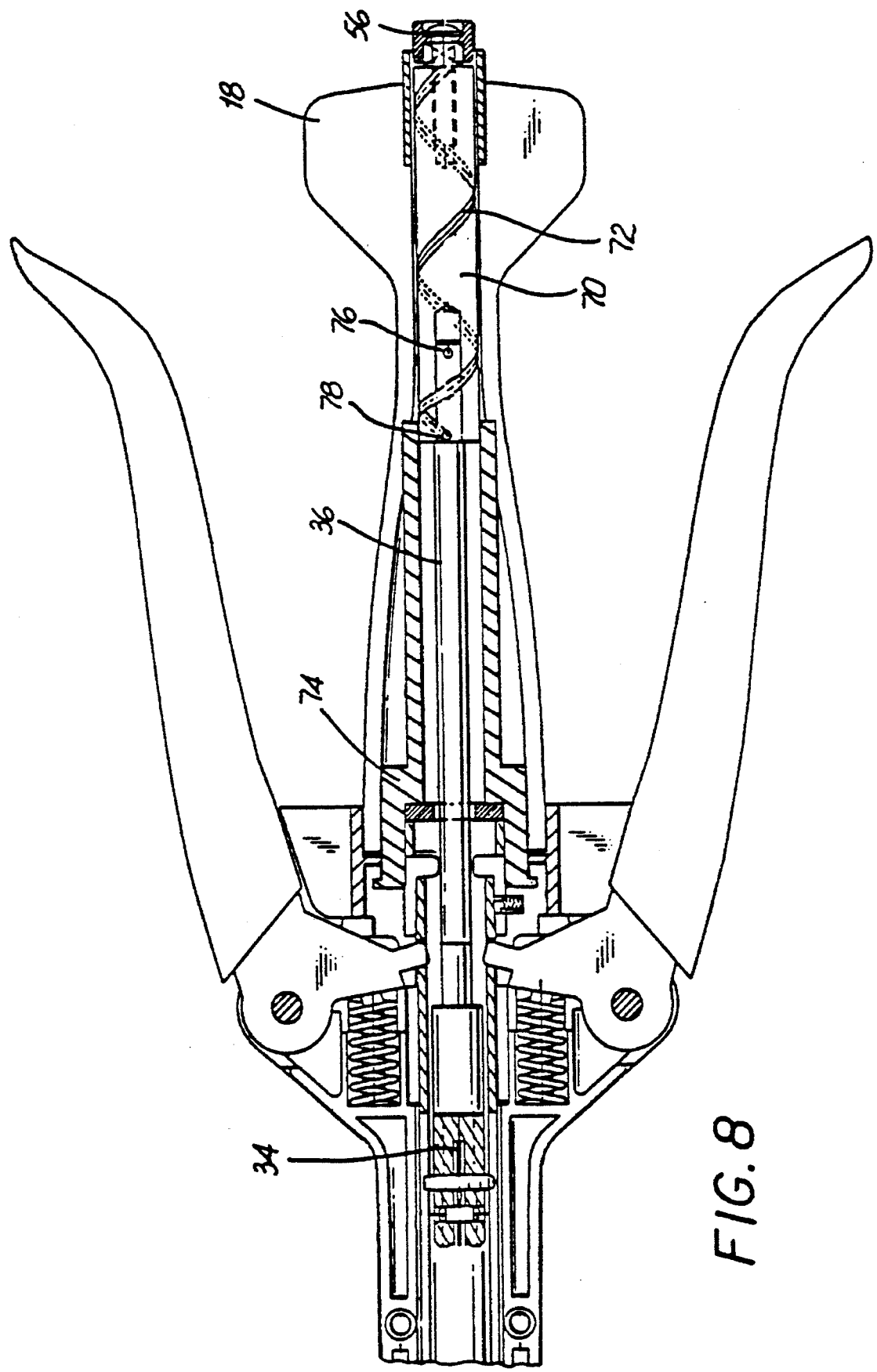
FIG. 8 illustrates a cross-sectional view of the apparatus of FIG. 7 showing the position of the cam member corresponding to the anvil member being positioned adjacent to the staple pusher member.

As grip member 18 is rotated, sleeve member 74 also rotates along with rotation pin 78. Rotation pin 78 causes helical groove 72 to ride over the pin 78 drawing cam member, and consequently inner rod member 36, in a proximal direction through bore 77 of grip member 18. As also seen in FIG. 8, rotation pin 78 rides over helical groove 72 at the first pitch to provide for a large approximation of the distance between anvil member 26 and staple pusher member 22. As cam member 70 moves the position shown in FIG. 8, the rotation pin 78 enters the smaller pitch section of helical groove 72, thus providing for fine adjustment of the distance between anvil member 26 and staple pusher member 22. When cam member 70 is in the position shown in FIG. 8, the flag 56 provides visual indication that the anvil member is in a position that will allow firing of the staples through the tissue to perform the circular anastomosis.

Figure 10:
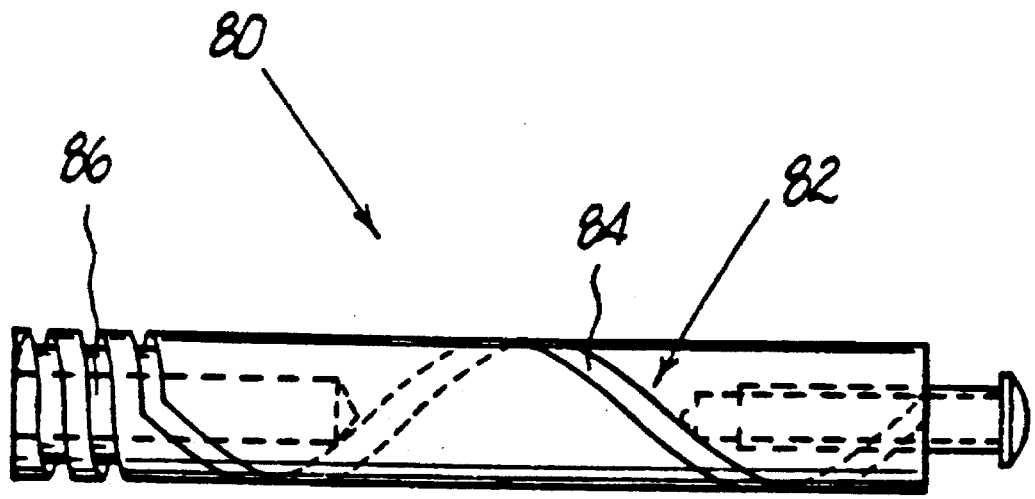
FIG. 10 illustrates a plan view of the cam member of the apparatus of FIGS. 11 and 12.
Figure 9:
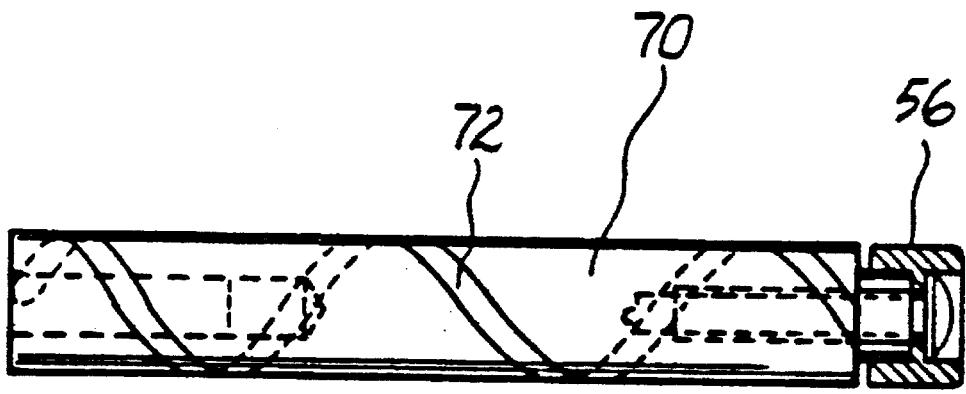
FIG. 9 illustrates a plan view of the cam member of the apparatus of FIGS. 7 and 8.
Figure 11:
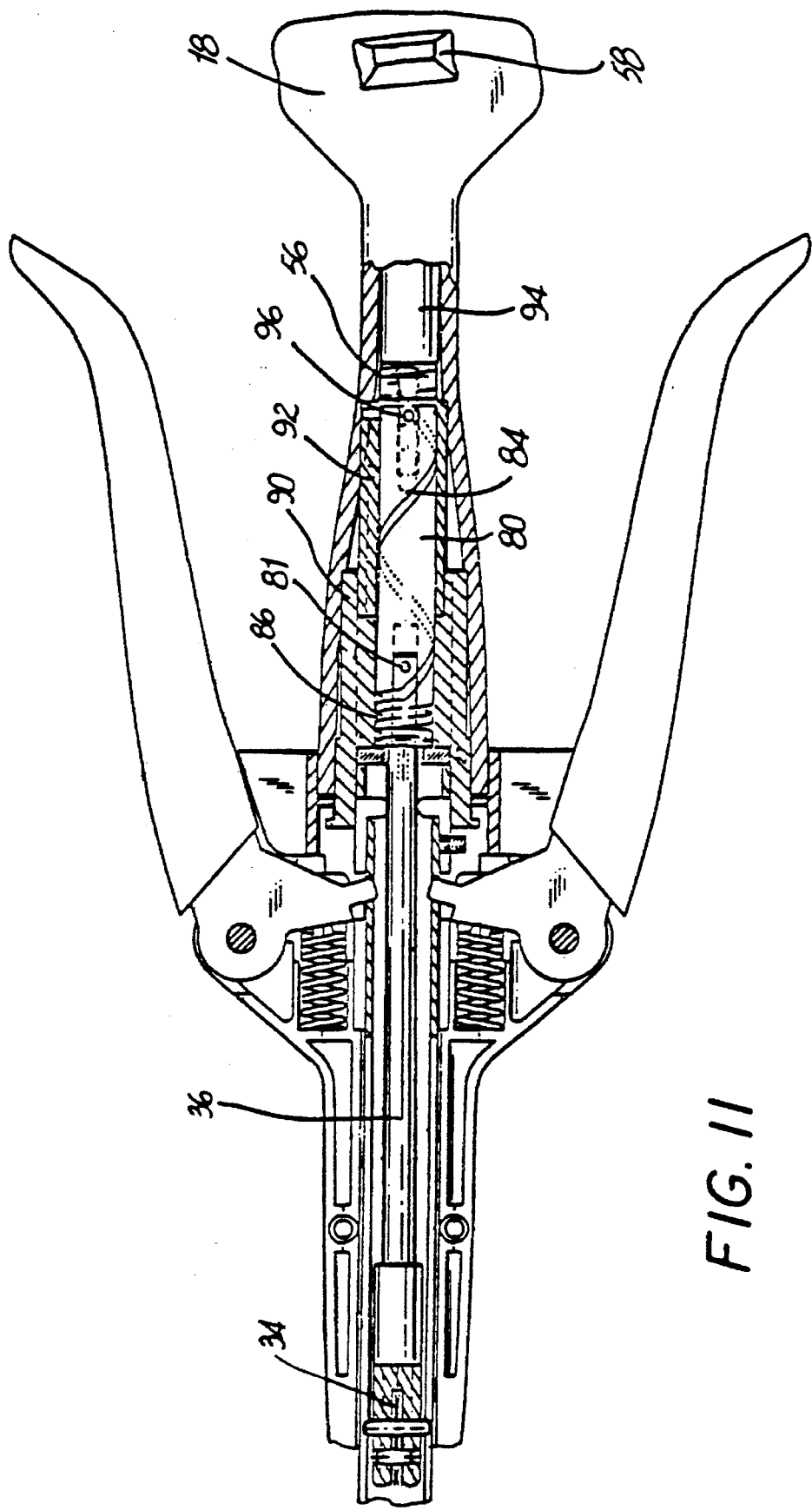
FIG. 11 illustrates a cross-sectional view of an alternate embodiment of the apparatus of FIG. 7 in which a cam member having a dual pitch helical groove is shown corresponding to the, position where the anvil member is located away from the staple pusher member.
Figure 12:
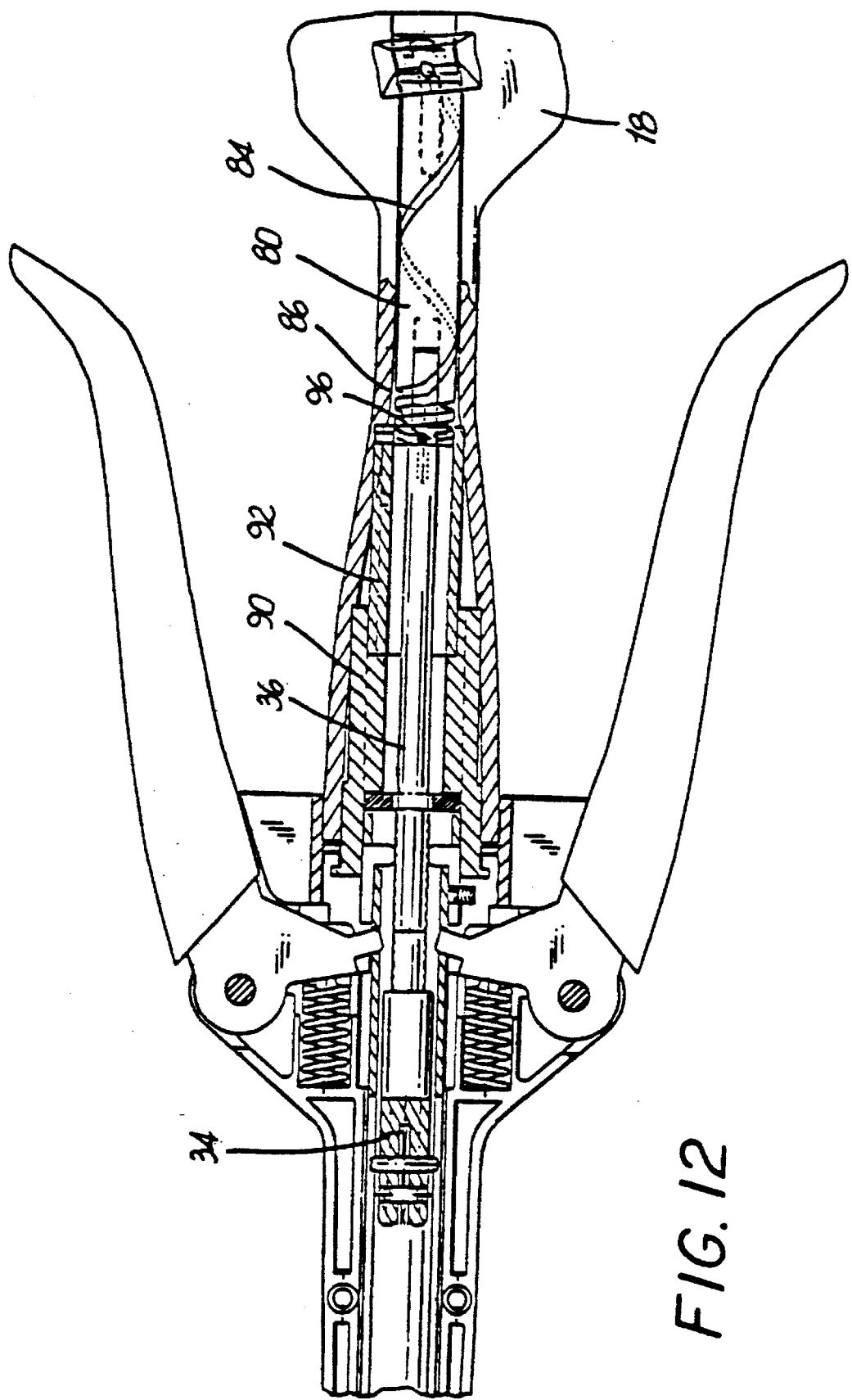
FIG. 12 illustrates a cross-sectional view of the apparatus of FIG. 11 in which the cam member is shown in a position corresponding to the anvil member being positioned adjacent to the staple pusher member.

FIG. 9 illustrates cam member 70 as described in FIGS. 7 and 8, and FIG. 10 illustrates an alternate embodiment of cam member 80 which is described in relation to FIGS. 11 and 12. Cam member 80 is provided with a helical groove 82 having a dual pitch. The first pitch 84 is greater than the second pitch 86, so that first pitch 84 provides for coarse adjustment or a large approximation of the anvil member 26 towards staple pusher member 22, while second pitch 86 provides for fine adjustment or incremental movement of the anvil member 26 towards staple pusher member 22. The operation of cam member 80 is illustrated in FIGS. 11 and 12, and is similar to that as described for FIGS. 7 and 8 previously.

As seen in FIG. 11, cam member 80 is positioned within rotatable bushing 90 and rotatable sleeve member 92. Cam member 80 is secured to inner rod 36 as described above, such as by pin 81. A rotation pin 96 is provided which is operably secured to rotatable sleeve 92, so that upon rotation of grip member 18, helical groove 82 begins to ride over pin member 96 at first pitch 84. Cam member 80 begins to slide rearwardly in bore 94, thus drawing inner rod member 36 and flexible member 34 in a proximal direction. As cam member 80 reaches a point where rotation pin 96 is at the end of first pitch 84, anvil member 26 is positioned adjacent staple pusher member 22. Further rotation of grip member 18, as seen in FIG. 12, causes second pitch 86 to ride over pin 96 to provide for fine adjustment of the distance between anvil member 26 and staple pusher member 22. Flag 56 appears in flag window 58 to provide a visual indication of the position of anvil member 26 with respect to staple pusher member 22.

Figure 13:
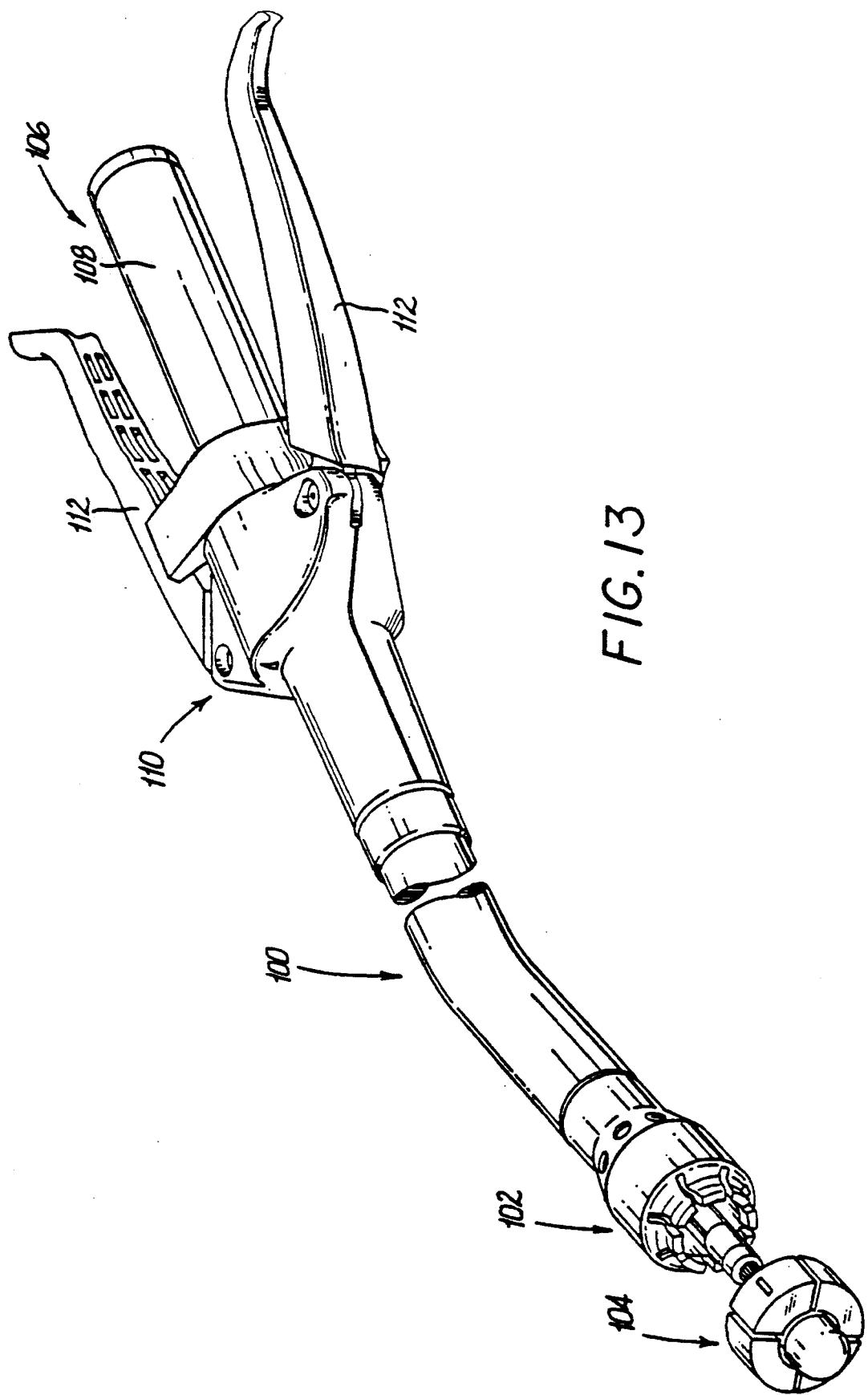
FIG. 13 illustrates a perspective view of an alternate embodiment of the apparatus of FIG. 1.

Turning now to FIG. 13, there is illustrated an alternate embodiment of the instrument 100 having the adjustable closure mechanism of the present invention. Instrument 100 includes a fastener assembly 102 which may comprise, for example, an anastomosis ring assembly for engagement with a member 104. Member 104 operates in a manner similar to anvil member 26 described above. Instrument 100 further includes an adjustable closing mechanism 106 which includes a grip member 108 rotatable in a manner described above with respect to grip member 18. Handle assembly 110 further includes actuating handle members 112 which function similar to that described above.

Figure 14:
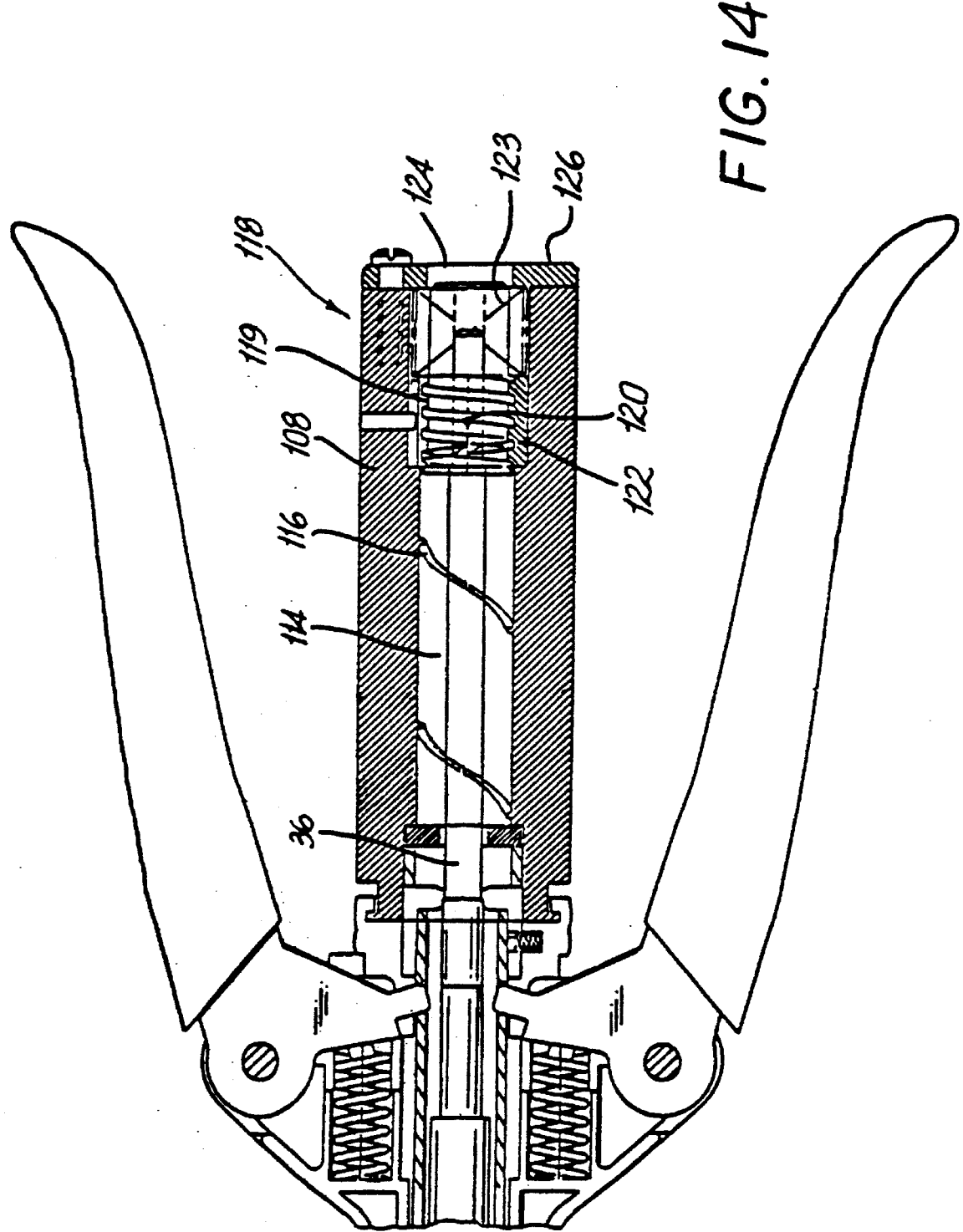
FIG. 14 illustrates a cross, sectional view of the apparatus of FIG. 13.

Turning to FIG. 14, there is illustrated a cross-section of the grip member 108 of FIG. 13 showing the adjustable closure mechanism. Inner rod member 36 is similar to that described above and is secured to advancing means 118 in a conventional manner, such as by pin 120. Advancing means 118 comprises a double threaded collar 119 whose initial position is at the left side of central bore 114 (in relation to FIG. 14). During rotation of grip member 108, double threaded collar 119 begins to ride in a proximal direction over internal threads 116 of bore 114 to the position shown on FIG. 14. Movement of double threaded collar 119 in this direction moves inner rod member 36 and consequently draws member 104 towards fastener assembly 102. Threads 116 engage collar 119 to provide for a coarse adjustment of the distance between fastener assembly 102 and member 104, to rapidly close the distance. Further rotation of grip member 108 causes dual threaded collar 119 to engage threaded bushing 122. As collar 119 engages bushing 122, bushing 122 is forced against spring 123 which results in a short dwell time as threaded collar 119 engages the threads of bushing 122. Bushing 122 provides for fine adjustment of the remaining distance between fastener assembly 102 and member 104. Continued rotation of grip member 108 closes the remaining distance between fastener assembly 102 and member 104, and a visual indication of the distance is provided by opening 124 at end cap 126.

Figure 15:
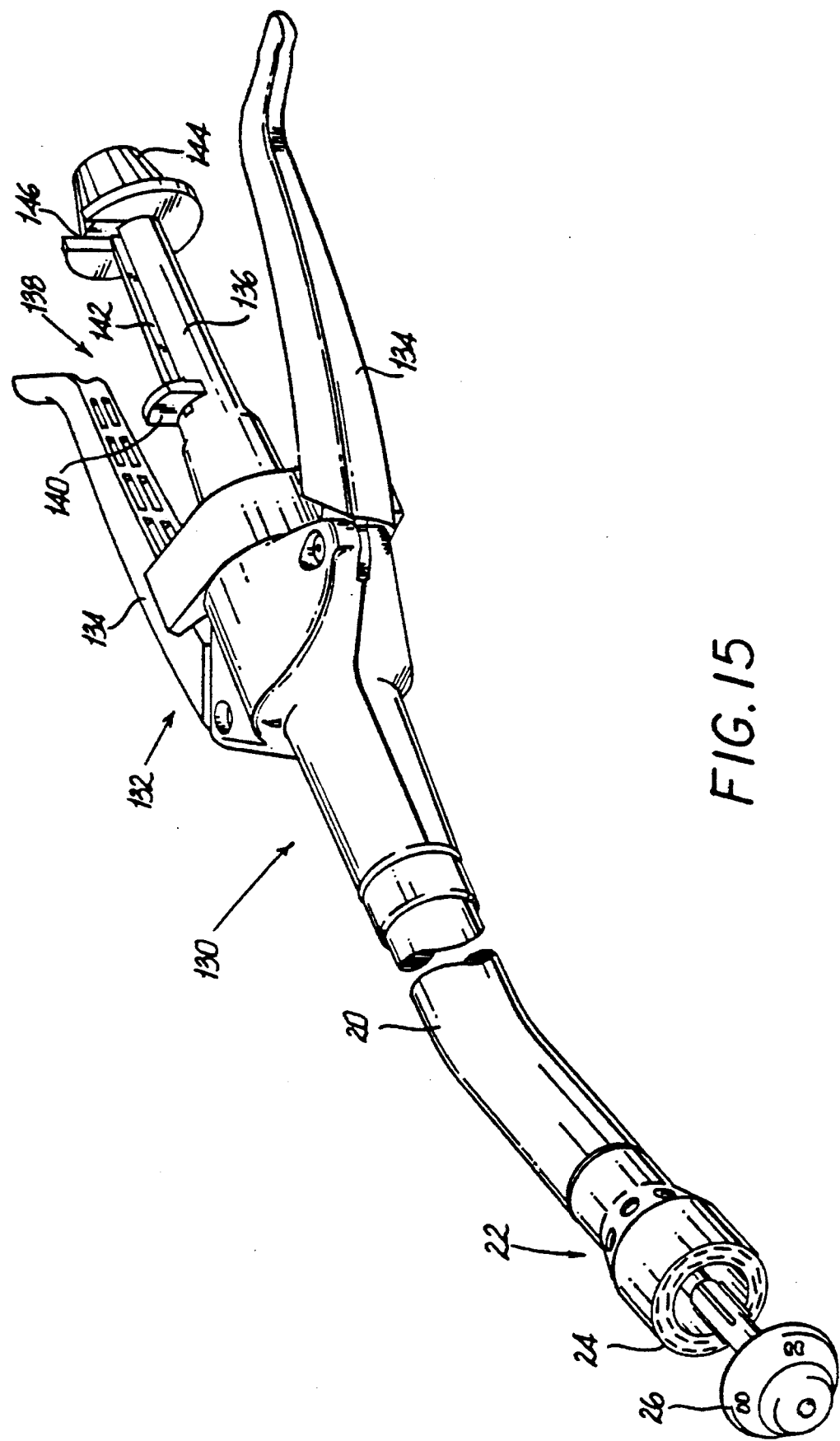
FIG. 15 illustrates a perspective view of an alternate embodiment of the apparatus of FIG. 1.

Turning now to FIG. 15, there is illustrated a surgical stapling apparatus having an alternate embodiment of the advancing means 138 of the present invention. Instrument 130 includes handle assembly 132 having pivotable handle members 134 similar to that described above. Extending from handle assembly 132 is tubular body portion 20 which terminates in staples pusher member 22 having anvil assembly 26 positioned adjacent thereto. Advancing means 138 includes a grip member 136 having a linearly slidable latch member 140 which slides along grip member 136 through slot 142. As best seen in FIGS. 16 and 17, latch member 140 is fixedly secured to inner rod member 36 which in turn is secured to flexible member 34 similar to that described above. As latch member 140 slides rearwardly towards knob 144, inner rod member 36 slides with it and provides a means for approximating anvil member 26 towards staple pusher member 22 over a large initial distance. As latch member 140 reaches knob 144, it is accommodated in a notch 146 which clears latch 140 from slot 142. As best seen in FIGS. 17a and 17b, once latch member 140 clears slot 142, knob 144 may be rotated, which rotates sleeve member 148 about threads 150 to provide for fine adjustment of the remaining distance between anvil member 26 and staple pusher member 22.

Figure 18:
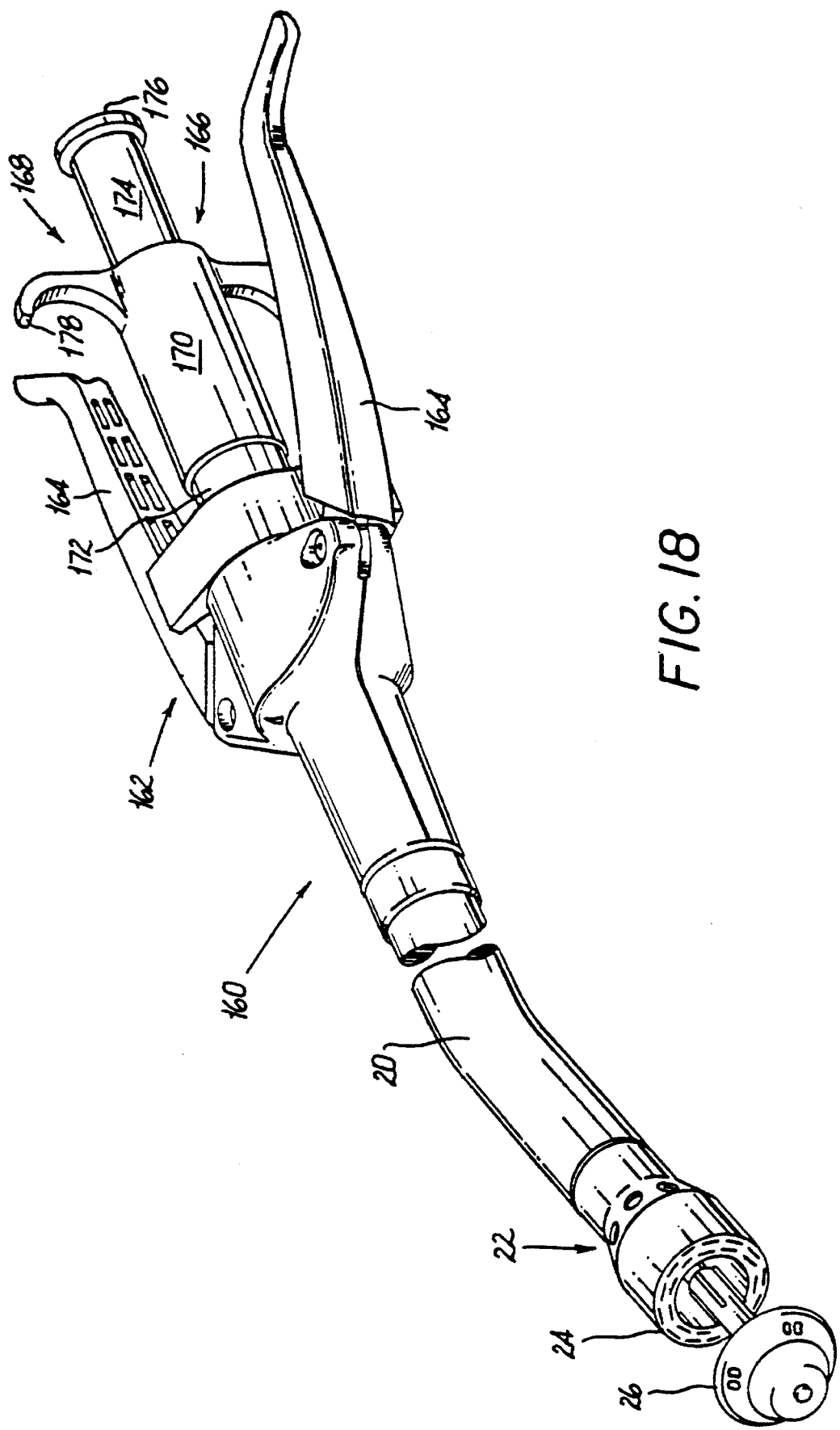
FIG. 18 illustrates a perspective view of an alternate embodiment of the apparatus of FIG. 1.

FIG. 18 illustrates a further embodiment of a surgical stapling apparatus having the adjustable closure mechanism of the present invention. Instrument 160 includes handle assembly 162 having pivotable handle members 164 similar to that described above. Extending from handle assembly 162 is tubular body portion 20 which terminates at the staple pusher member 22, having anvil member 26 positioned opposite thereto. Handle assembly 162 includes grip member 166 having finger grips 178, and advancing means 168.

Figure 20:
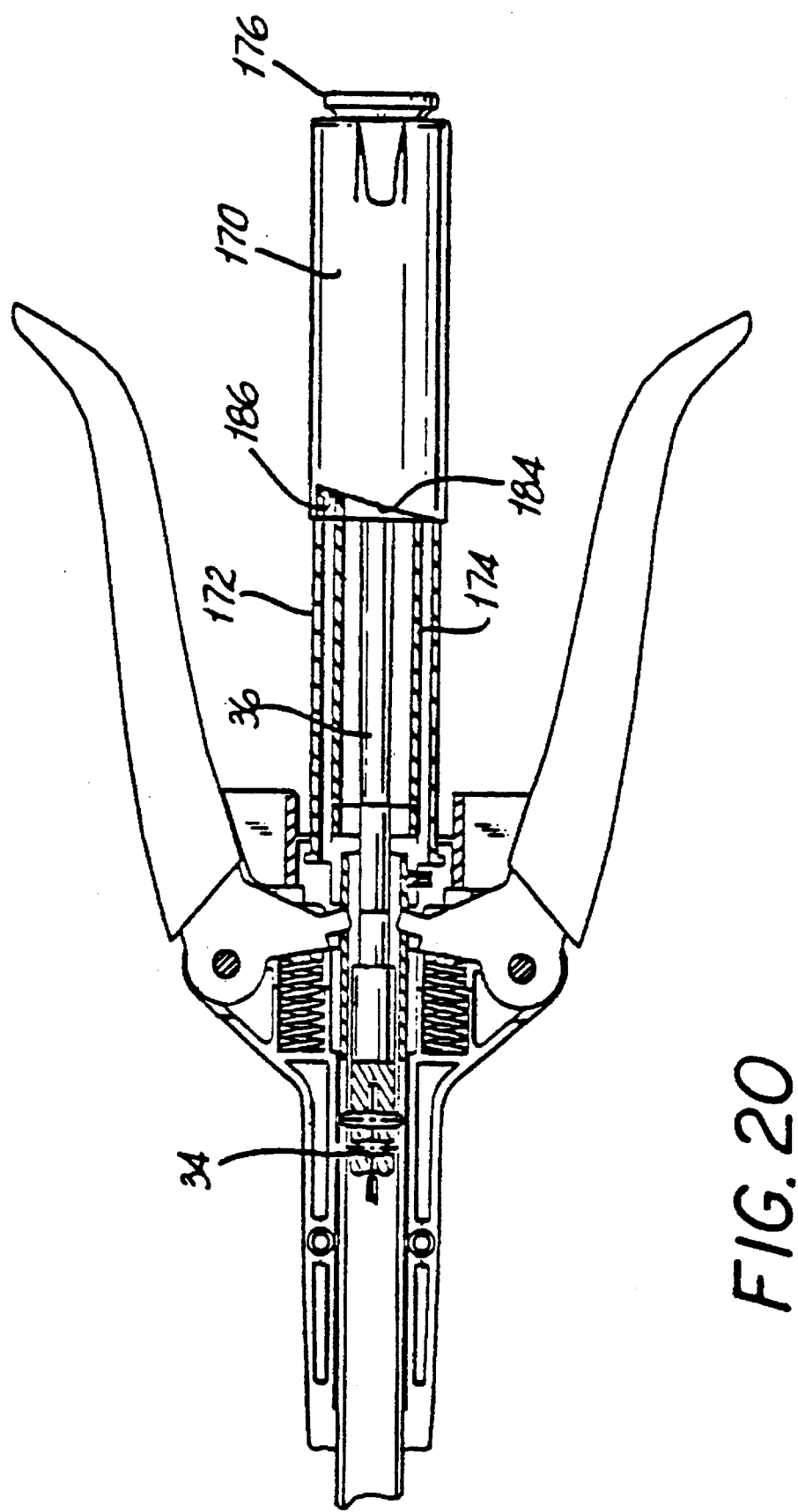
FIG. 20 illustrates a partial cross-sectional view of the apparatus of FIG. 18 in which advancing means is in a position corresponding to the anvil member being positioned adjacent to the staple pusher member.

As best seen in FIGS. 19a and 19b, inner rod member 36 is secured to a slidable telescopic outer cylinder 170 which slides over guide cylinder 172 and along guide rod 174. Outer cylinder 170 includes a pin 180 which slides along track 182 of guide rod 174. Movement of outer cylinder 170 is facilitated by finger grips 178. Outer cylinder 170 slides along guide rod 174 until it reaches stop member 176. As best seen in FIG. 20, once outer cylinder 170 reaches stop member 176, outer cylinder 170 may be rotated so that cam surface 184 rides along bearing surface 186 to provide for fine adjustment of the distance between anvil member 26 and staple pusher member 22.

Figure 21:
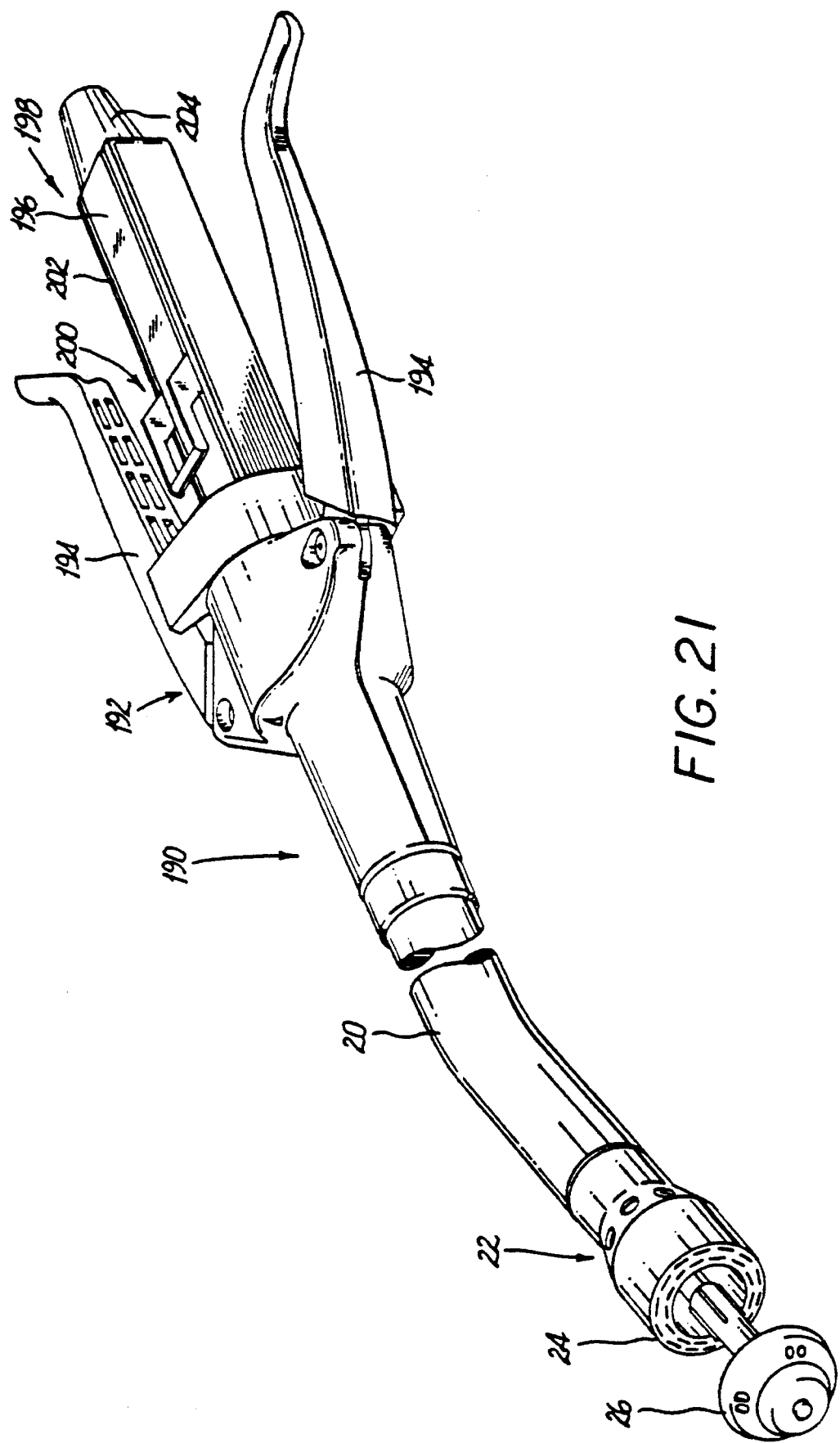
FIG. 21 illustrates a perspective view of an alternate embodiment of the apparatus of FIG. 1.
Figure 22A:
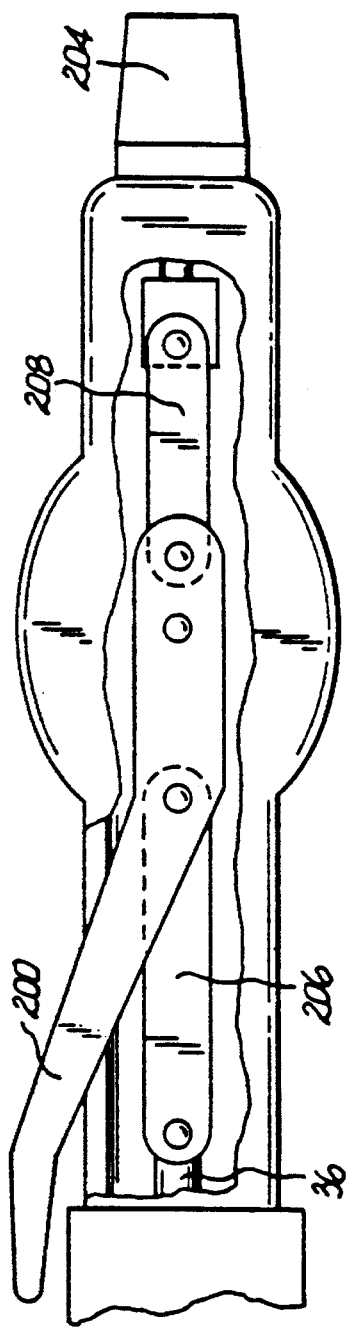
FIGS. 22a–22c illustrate a side schematic views showing the positioning of the lever mechanism of, FIG. 21 during actuation.
Figure 22B:
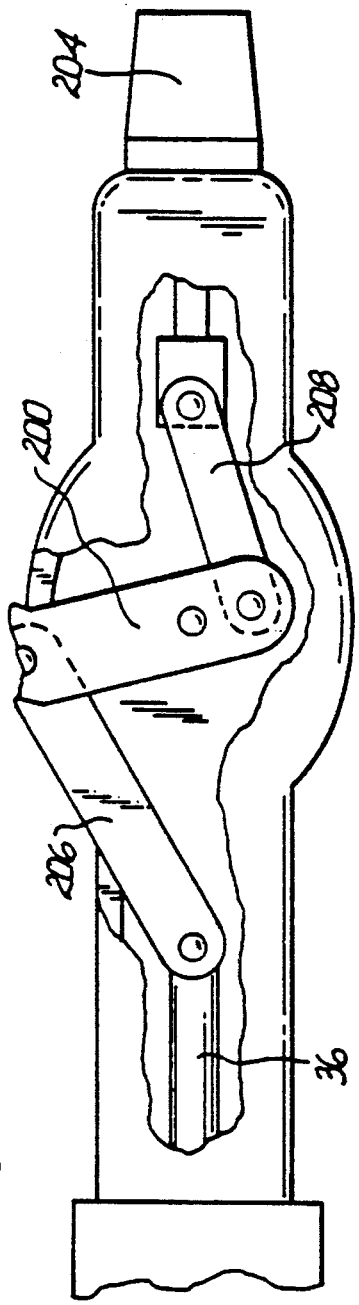
Figure 22C:
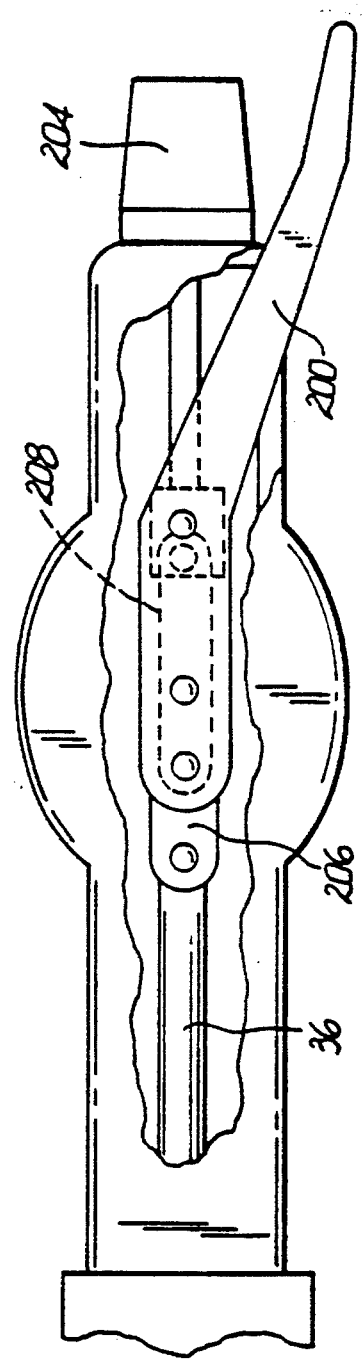

Turning now to FIG. 21, there is illustrated a surgical stapling instrument having an alternate embodiment of the adjustable closure mechanism of the present invention. Instrument 190 includes a handle assembly 192 which includes pivotable handle members 194 similar to that described above. Extending from handle assembly 192 is tubular body portion 20 which terminates in staple pusher mechanism 22 and includes anvil member 26 opposite staple pusher member 22. Handle assembly 192 includes a grip member 196 having advancing means 198 positioned thereon. Advancing means 198 essentially comprises a lever mechanism 200 which is pivotable through slots 202 over a longitudinal axis of the instrument as best seen in FIGS. 22a–22c. Knob member 204 is also part of advancing means 198.

As best seen in FIGS. 22a–22c, advancing means 198 comprises lever 200 and includes linkage mechanism 206 and 208. Linkage mechanism 206 is secured to inner rod member 36 for approximating the distance between anvil member 26 and staple pusher member 22. In use, lever 200 is pulled rearwardly as shown in FIG. 22b to move inner rod member 36 in a proximal direction. Lever 200 is pivoted over the longitudinal axis of the instrument and provides for coarse adjustment of the distance between anvil member 26 and staple pusher member 22, as best seen in FIG. 22c. Knob 204 may then be rotated to provide for fine adjustment of the distance between anvil member 26 and staple pusher member 22. FIGS. 23a and 23b further show a schematic view of the lever and linkage mechanism.

Figure 24:
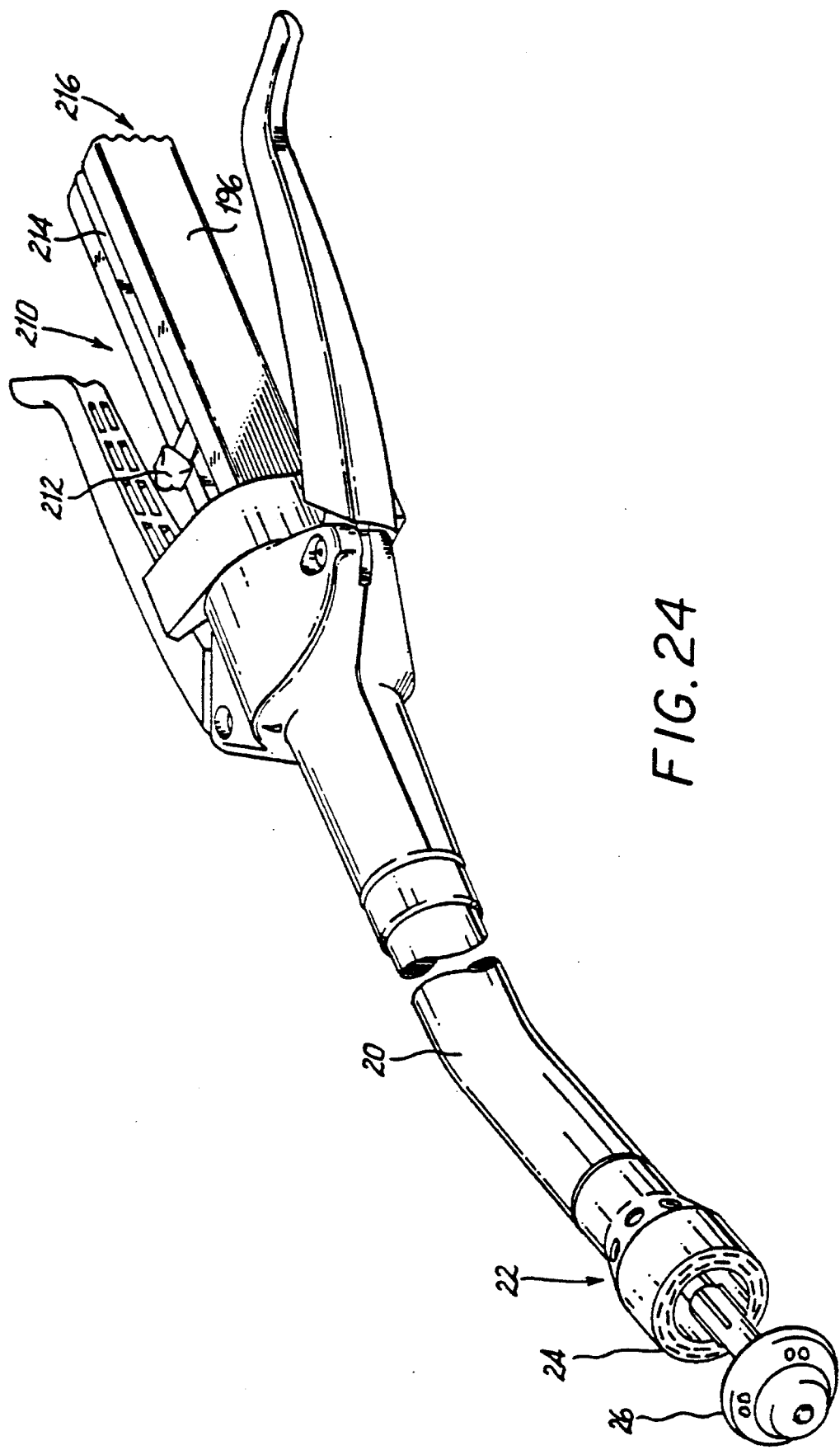
FIG. 24 illustrates a perspective view of an alternate embodiment of the apparatus of FIG. 21.

FIG. 24 illustrates an alternate embodiment of the lever mechanism comprising the advancing means of FIG. 21. FIG. 24 illustrates advancing means 210 which includes a lever mechanism 212 which rides a slot 214 in grip member 196. Grip member 196 further includes a ratchet means 216 whose function will be described below.

Figure 26A:
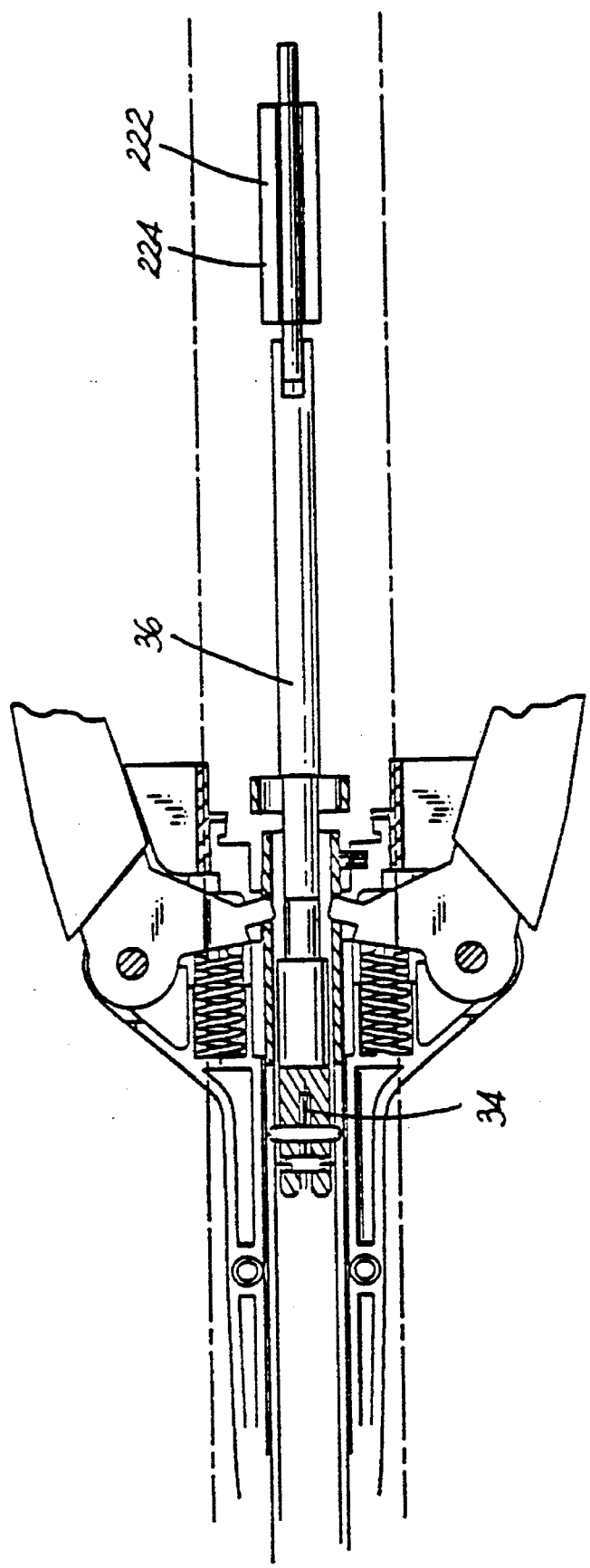
FIGS. 26a and 26b illustrate top schematic views of the lever mechanism of FIG. 24 before and after actuation.
Figure 26B:
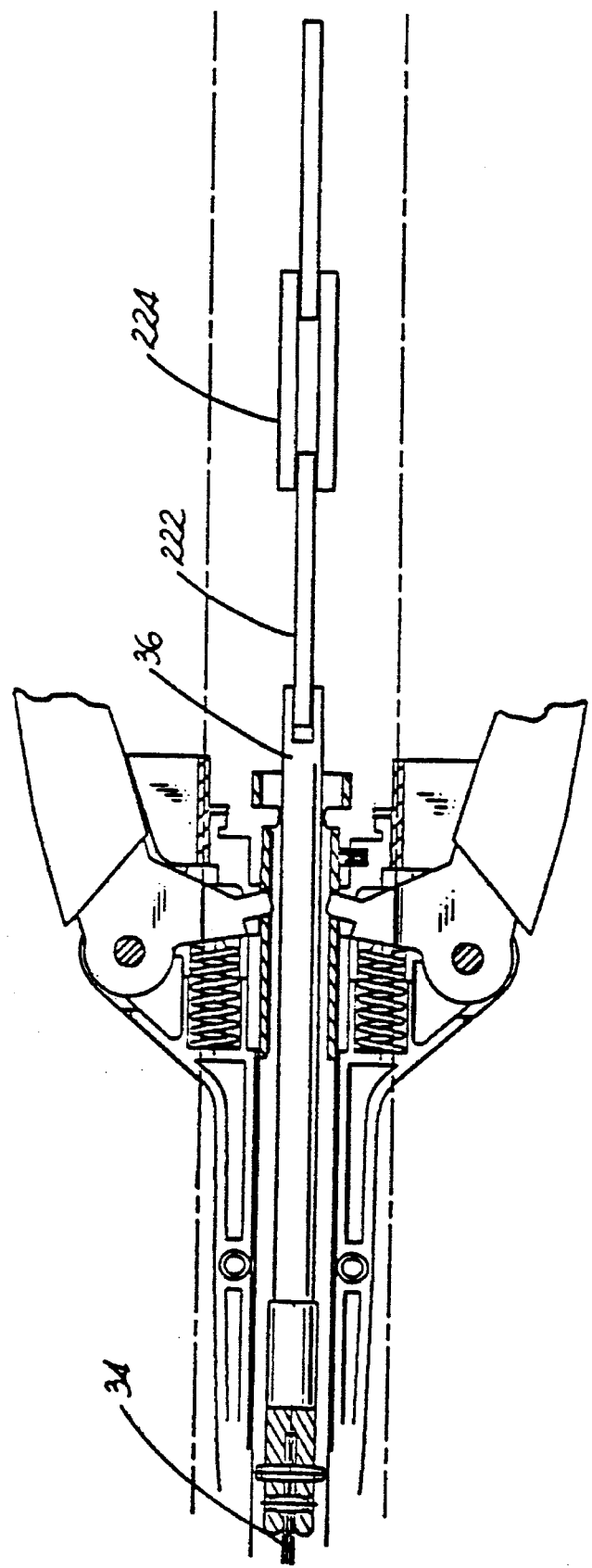

Turning now to FIGS. 25a–25c, there is shown the movement of lever mechanism 212. Lever mechanism 212 is operably connected to inner rod member 36 by linkage member 222. Advancing means 210 also includes linkage member 224. Lever mechanism 212 is pivoted over the longitudinal axis of grip member 196 in a manner similar to that described above in relation to FIG. 21. As lever mechanism 212 reaches the position shown in FIG. 25b, pawl detent 220 engages rack member 218 to provide for incremental adjustment of the distance between anvil member 26 and staple pusher member 22. FIGS. 26a and 26b illustrate a schematic view of the linkage mechanism of the lever mechanism of FIG. 24.

It should be noted that the various closure mechanisms described herein can be utilized in stapling instruments as well as other anastomosis instruments such as those having a ring assembly as shown in FIG. 13.

The surgical stapling of fastening instrument employing the adjustable closure mechanism of the present invention is a device which may be operated to quickly approximate the distance between the anvil member and the staple pusher member, followed by an additional movement to provide for fine adjustment of the distance between the anvil member and the staple pusher member. The device is quick and easy to use and expedites the surgical procedure.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical apparatus for applying an annular array of staples comprising:

a tubular body portion;

a staple pusher disposed at a distal end of the body portion, the staple pusher configured to expel an annular array of staples;

an anvil disposed at a distal end of the body portion and positioned opposite the array of staples, wherein the anvil deforms the staples upon expulsion of the staples; and an anvil moving mechanism positioned at a proximal end portion of the body portion, the anvil moving mechanism moving the anvil towards and away from the array of staples, wherein movement of the anvil moving mechanism by a first amount moves the anvil a first distance towards the array of staples and a subsequent, equal movement of the mechanism moves the anvil a second distance towards the array of staples, wherein the first distance is greater than the second distance.

2. The apparatus according to claim 1, wherein the anvil moving mechanism includes a rotatable grip member rotatably mounted to the proximal end portion of the apparatus.

3. The apparatus according to claim 1, wherein the tubular body portion is curved.

4. The apparatus according to claim 1, further comprising at least one movable handle pivotally associated with the body portion, the movable handle being operatively associated with the staple pusher, wherein movement of the at least one handle expels the annular array of staples.

5. The apparatus according to claim 1, further comprising at least one flexible member at least partially disposed within the tubular body portion for transmitting longitudinal tension and longitudinal motion, relative to the tubular body portion, to the anvil upon movement of the anvil moving mechanism.

6. The apparatus according to claim 1, wherein the anvil moving mechanism further includes a cam member having a helical groove positioned within the apparatus, wherein movement of the anvil moving mechanism causes longitudinal movement of the cam member.

7. The apparatus according to claim 6, wherein the helical groove has at least one portion with a first helical pitch and another portion with a second helical pitch, the first helical pitch being different than the second helical pitch.

8. A surgical stapling apparatus for applying an annular array of staples comprising:

a tubular body portion;

a staple pusher disposed at a distal end of the body portion the staple pusher configured to expel an annular array of staples;

an anvil disposed at a distal end of the body portion and positioned opposite the array of staples, wherein the anvil deforms the staples upon expulsion of the staples; and a rotatable anvil moving mechanism positioned at a proximal end portion of the body portion, the anvil moving mechanism moving the anvil towards and away from the array of staples and including a cam member having a helical groove, wherein rotation of the anvil moving mechanism by a first amount moves the anvil a first distance towards the array of staples and a subsequent, equal rotation of the anvil moving mechanism moves the anvil a second distance towards the array of staples, wherein the first distance is greater than the second distance.

9. The apparatus according to claim 8, wherein the tubular body portion is curved.

10. The apparatus according to claim 8, further comprising at least one movable handle pivotally associated with the body portion, the movable handle being operatively associated with the staple pusher, wherein movement of the at least one handle expels the annular array of staples.

11. The apparatus according to claim 8, further comprising at least one flexible member at least partially disposed within the tubular body portion for transmitting longitudinal tension and longitudinal motion, relative to the tubular body portion, to the anvil upon movement of the anvil moving mechanism.

12. A surgical apparatus for applying an annular array of staples comprising:

a tubular body portion;

a staple pusher disposed at a distal end of the body portion the staple pusher configured to expel an annular array of staples;

an anvil disposed at a distal end of the body portion and positioned opposite the array of staples, wherein the anvil deforms the staples upon expulsion of the staples; and an anvil moving mechanism positioned at a proximal end portion of the body portion, the anvil moving mechanism moving the anvil towards and away from the array of staples;

wherein a first portion of the anvil moving mechanism has a first configuration to move the anvil a first distance towards the array of staples and a second portion of the anvil moving mechanism has a second configuration to move the anvil a second distance towards the array of staples, wherein the first configuration of the anvil moving mechanism is different than the second configuration and wherein the first distance is greater than the second distance.

13. The apparatus according to claim 12, wherein the first configuration of the first portion of the anvil moving mechanism is a helical groove having a first helical pitch and the second configuration of the second portion of the anvil moving mechanism is a helical groove having a second helical pitch, the first helical pitch being different than the second helical pitch.

14. The apparatus according to claim 12, wherein the anvil moving mechanism includes a cam member having a helical groove.

15. The apparatus according to claim 14, wherein the first configuration is a first helical pitch of the helical groove and a second configuration is a second, different helical pitch of the helical groove.

16. The apparatus according to claim 15, wherein the anvil moving mechanism includes a rotatable grip member rotatably mounted to the proximal end portion of the apparatus.

17. The apparatus according to claim 16, wherein the tubular body portion is curved.

18. The apparatus according to claim 17, further comprising at least one movable handle pivotally associated with the body portion, the movable handle being operatively associated with the staple pusher, wherein movement of the at least one handle expels the annular array of staples.

19. The apparatus according to claim 12, further comprising at least one flexible member at least partially disposed within the tubular body portion for transmitting longitudinal tension and longitudinal motion, relative to the tubular body portion, to the anvil upon movement of the anvil moving mechanism.

* * * * *